United States Patent [19]
Houghten et al.

[11] Patent Number: 5,912,231
[45] Date of Patent: Jun. 15, 1999

[54] SUBSTITUTION ANALOGUES OF MAGAININ PEPTIDES

[75] Inventors: Richard A. Houghten, Solana Beach; Julio H. Cuervo, Cardiff, both of Calif.

[73] Assignee: Scripps Clinic and Research Foundation

[21] Appl. No.: 08/338,882

[22] Filed: Nov. 14, 1994

Related U.S. Application Data

[63] Continuation of application No. 07/615,125, Nov. 15, 1990, abandoned, which is a continuation-in-part of application No. 07/376,754, Jul. 7, 1989, abandoned.

[51] Int. Cl.⁶ .......................... A61K 38/10; A61K 38/16; C07K 7/08; C07K 14/00
[52] U.S. Cl. ................. 514/13; 514/14; 514/15; 530/326; 530/327
[58] Field of Search .................. 530/324–328; 514/12–17

[56] References Cited

U.S. PATENT DOCUMENTS

| | | | |
|---|---|---|---|
| 4,810,777 | 3/1989 | Zasloft | 530/326 |
| 4,962,277 | 10/1990 | Cuervo et al. | 514/14 |
| 5,045,531 | 9/1991 | Berkowitz et al. | 514/12 |
| 5,208,220 | 5/1993 | Berkowitz | 514/13 |
| 5,217,956 | 6/1993 | Zasloff et al. | 514/13 |
| 5,221,664 | 6/1993 | Berkowitz et al. | 514/6 |
| 5,221,732 | 6/1993 | Chen et al. | 530/326 |
| 5,235,038 | 8/1993 | Blondelle et al. | 530/324 |

FOREIGN PATENT DOCUMENTS 8806597  9/1988  WIPO .

OTHER PUBLICATIONS

Chen et al. 'Magainnin 2 Amide And Analogues' Febs Letters, vol. 249, No. 2, pp. 219–223, Jun. 1989.
Cuervo et al. 'The Magainis: Sequence Factors Relavant To Increased Antimicrobial Activity And Decreased Hemolytic Activity' Peptide Research, vol. 1, No. 2 pp. 81–86, 1988.
Spatol, AF. Chemistry And Biochemistry Of Amino Acids, Peptides And Proteins. New York: Marcel Dekker, Inc., ppl 284–285, 1983.
Chen, et al, vol. 236, No. 2, pp. 462–466, FEB, 1988.
Cuervo, et al, vol. 1, No. 2, Peptide Research, 1988.
Christensen, et al, vol. 85, Proc. Natl. Acad. Sci, pp. 5072–5076).
Zasloff et al., *Proc. Natl. Acad. Sci., USA*, 85:910–913 (1988).
Chen et al., *FEB*, 236(2):462–466 (Aug. 1988).
Cuervo et al., *Peptide Research*, 1(2):81–86 (Nov.–Dec. 1988).
Cuervo et al., Peptides, *Chemistry, Structure and Biology*, Proceedings of the Eleventh American Peptide Symposium, Jul. 9–14, 1989, La Jolla, California, U.S.A.; Rivier and Marshall eds., ESCOM, Leiden (1990), pp. 124–126.
Derwent (WPIL), AN–90–019331 [03]; and JP–A–88 127 177 (Sagami Chem. Res. Centre) May 26, 1988; Abstract.
Tjoeng et al., *Int. J. Peptide Protein Res.*, 35:141–146 (1990).
Chen et al, vol. 236, No. 2, 462–466, 1988.
Cuervo, et al, Peptides, pp. 124–126, 1990.

*Primary Examiner*—Cecilia J. Tsang
*Assistant Examiner*—Anish Gupta
*Attorney, Agent, or Firm*—Welsh & Katz, Ltd.

[57] ABSTRACT

A compound comprising a Magainin I or Magainin II peptide wherein at least one substitution may be made for certain amino acid residues with other amino acid residues, said peptides known as substitution analogues.

In addition to such substitutions, there can be included within the scope of the invention analogues wherein at least one of amino acid residues 15 and 23 may have been deleted as well, and wherein substitutions were made in the remaining peptide chain. Certain substituttion analogues within the scope of the present invention have been shown to possess increased biological activity.

26 Claims, No Drawings

SUBSTITUTION ANALOGUES OF MAGAININ PEPTIDES

This application is a continuation of application Ser. No. 07/615,215, filed Nov. 15, 1990, now abandoned, which intern is a continuation-in-part of application Ser. No. 376,754, filed Jul. 7, 1989 now abandoned.

This invention was made with government support under Contract No. DIR-8713707 by NSF. The government has certain rights in the invention.

This invention relates to a class of biologically active peptides known as magainins. More particularly, this invention relates to analogues of magainin peptides wherein at least one amino acid residue in the peptide has been substituted with another amino acid residue, with said analogues being commonly referred to as "substitution analogues."

In accordance with an aspect of the present invention, there is provided a compound comprising an analogue of Magainin I peptide or Magainin II peptide. The Magainin I or Magainin II peptide is in an amide or carboxy terminated form. Magainin I is represented by the following structural formula using the single letter amino acid code and the numbers below each amino acid residues refer to the position of the residue in the peptide.
G I G K F L H S A G K F G K A F V G E I M K S 1 2 3 4 5 6 7 8 9 10 11 12 13 14 15 16 17 18 19 20 21 22 23
Gly Ile Gly Lys Phe Leu His Ser Ala Gly Lys Phe Gly Lys Ala Phe Val Gly Glu Ile Met Lys Ser (SEQ ID NO:1)
Magainin II is represented by the following structural formula using the single letter amino acid code and the numbers below each amino acid residue refer to the position of the residue in the peptide:
G I G K F L H S A K K F G K A F V G E I M N S 1 2 3 4 5 6 7 8 9 10 11 12 13 14 15 16 17 18 19 20 21 22 23
Gly Ile Gly Lys Phe Leu His Ser Ala Lys Lys Phe Gly Lys Ala Phe Val Gly Glu Ile Met Asn Ser (SEQ ID NO:2)
The Magainin I or Magainin II peptide is substituted in at least one of positions 1–23. The substituted amino acid residues which may be employed in each of positions 1–23 are shown in the following table:

| Residue No. | Substituted Residue |
| --- | --- |
| 1 | Lys, Ala |
| 2 | Lys, Ala, D—Ile, Arg, Leu, Val, His, Met |
| 3 | Lys, Ala, Trp, Arg, His |
| 4 | D—Lys, Ala, Arg, His |
| 5 | D—Phe, Ala, Lys, Trp, Leu, Ile, Val, Met |
| 6 | D—Leu, Lys, Ala, Ile, Val, Met |
| 7 | Lys, D—His, Ala, Arg, Ile, Val, Met |
| 8 | Ala, Lys, D—Ser, Trp, Met, Ile, Arg, His, Thr, Leu, Val |
| 9 | Lys, D—Ala, Trp, Arg, His, Leu, Ile, Val |
| 10 | D—Lys, Lys Ala, Trp, Arg, His, Leu, Ile, Val |
| 11 | D—Lys, Arg, His |
| 12 | D—Phe, Lys, Trp, Arg, His |
| 13 | Ala, Lys, Trp, Met, Arg, His, Phe, Leu, Ile, Val |
| 14 | Ala, D—Lys, Arg, His |
| 15 | Lys, Trp, D—Ala, Arg, His, Phe |
| 16 | Ala, Lys, D—Phe, Ile, Val, Met, Leu |
| 17 | Ala, Lys, D—Val, Trp, Arg, His, Met, Leu |
| 18 | Ala, Lys, Trp, Arg, His, Leu, Met |
| 19 | Ala, Lys, D—Glu, Gly, Arg, His, Leu Ile, Phe, Asn |
| 20 | D—Ile, Ala, Lys, Trp, Leu, Phe, Val, Met |
| 21 | Lys, Pro, Ala, His, Leu, Arg, Ile, Phe |
| 22 | Lys, Ala, D—Asn, Gln, Arg, His |

| Residue No. | Substituted Residue |
| --- | --- |
| 23 | D—Ser, Lys, Ala, Thr, Gly, Leu, Ile, Gln, Asn |

Preferably, the substituted amino acid residues are as follows:

| Residue No. | Substituted Residues |
| --- | --- |
| 1 | Lys, Ala |
| 2 | Lys, Ala, D—Ile |
| 3 | Lys, Ala, Trp |
| 4 | D—Lys, Ala |
| 5 | D—Phe, Ala, Lys, Trp |
| 6 | D—Leu, Lys, Ala |
| 7 | Lys, D—His, Ala |
| 8 | Ala, Lys, D—Ser, Trp |
| 9 | Lys, D—Ala, Trp |
| 10 | D—Lys, Lys Ala, Trp |
| 11 | D—Lys |
| 12 | D—Phe, Lys, Trp |
| 13 | Ala, Lys, Trp |
| 14 | Ala, D—Lys |
| 15 | Lys, Trp, D—Ala |
| 16 | Ala, Lys, D—Phe |
| 17 | Ala, Lys, D—Val, Trp |
| 18 | Ala, Lys, Trp |
| 19 | Ala, Lys, D—Glu |
| 20 | D—Ile, Ala, Lys, Trp |
| 21 | Lys, Pro, Ala |
| 22 | Lys, Ala, D—Asn |
| 23 | D—Ser, Lys, Ala |

It is to be understood that for purposes of the present invention, that the tryptophan residues may be protected with a formyl group or be unprotected. The phenylalanine residues, whether such residue is present in its normal position, or employed as a substitution residue, may be normal phenylalanine residue or an iodinated phenylalanine residue.

The methionine residues, whether each such residue is present in its normal position, or employed as a substitution residue, may be a normal methionine residue or a methionine sulfoxide residue.

In accordance with one embodiment, the peptide is a Magainin I peptide, and at least one of amino acid residues 8, 10, 13, 16, 18 and 19 is substituted with an alanine residue. In another embodiment, the Magainin I peptide has alanine residue substitutions at each of amino acid residues 3, 8, 16, 19 and 23.

In accordance with another embodiment, the Magainin I peptide has alanine residue substitution at four of amino acid residues 3, 8, 16, 19 and 23, and the remaining one of these residues is substituted with a lysine residue.

In accordance with yet a further embodiment, amino acid 21 of a Magainin I peptide is substituted with a proline residue.

In accordance with another embodiment, at least one of amino acid residues 3, 7, 8, 10, 18–21, and 23 of Magainin I is substituted with a lysine residue.

In accordance with another embodiment, amino acid residues 3, 8, 9, 19 and 23 of Magainin I are each substituted with a lysine residue and amino acid residue 16 is substituted with an alanine residue.

In accordance with another embodiment, at least one of amino acid residues 2, 4, 19, or 23 of Magainin I is a D-amino acid residue, whose structure corresponds to that of the L-amino acid residue originally present in Magainin I.

In accordance with a further embodiment, at least one and amino acid residues 3, 5, 8, 10, 12, 13, 15, 18, and 20 of Magainin I is substituted with a protected tryptophan residue, wherein the protecting group is preferably a formyl group. In accordance with another embodiment, at least one of amino acid residues 9, 13, 15 and 17 of Magainin I is substituted with an unprotected tryptophan residue.

In accordance with another embodiment, the peptide is a Magainin II peptide, and at least one of amino acid residues 1–8, 10, 13, 14, 16 and 18–23 is an alanine residue.

In accordance with another embodiment, at least one of amino acid residues 1–3, 5–9, 12, 13 and 15–23 of Magainin II is a lysine residue.

In accordance with yet another embodiment, at least one of amino acid residues 2,4–12, 15–17, 19, 20, 22 and 23 of Magainin II is substituted with a D-amino acid residue whose structure corresponds to that of the L-amino acid residue originally present in Magainin II.

In accordance with another aspect of the present invention, there is provided an analogue of Magainin I or Magainin II peptide, said Magainin I or Magainin II peptide being in an amide-terminated or carboxy-terminated form and having the structural formulas hereinabove described, and wherein at least one of amino acid residues 15–23 is omitted and at least one of the remaining amino acid residues is substituted. The substituted amino acid residues which may be employed in at least one of positions 1–23 are shown in the following table:

| Residue No. | Substituted Residue |
| --- | --- |
| 1 | Lys, Ala |
| 2 | Lys, Ala, D—Ile, Arg, Leu, Val, His, Met |
| 3 | Lys, Ala, Trp, Arg, His |
| 4 | D—Lys, Ala, Arg, His |
| 5 | D—Phe, Ala, Lys, Trp, Leu, Ile, Val, Met |
| 6 | D—Leu, Lys, Ala, Ile, Val, Met |
| 7 | Lys, D—His, Ala, Arg, Ile, Val, Met |
| 8 | Ala, Lys, D—Ser, Trp, Met, Ile, Arg, His, Thr, Leu, Val |
| 9 | Lys, D—Ala, Trp, Arg, His, Leu, Ile, Val |
| 10 | D—Lys, Lys |
|  | Ala, Trp, Arg, His, Leu, Ile, Val |
| 11 | D—Lys, Arg, His |
| 12 | D—Phe, Lys, Trp, Arg, His |
| 13 | Ala, Lys, Trp, Met, Arg, His, Phe, Leu, Ile, Val |
| 14 | Ala, D—Lys, Arg, His |
| 15 | Lys, Trp, D—Ala, Arg, His, Phe |
| 16 | Ala, Lys, D—Phe, Ile, Val, Met, Leu |
| 17 | Ala, Lys, D—Val, Trp, Arg, His, Met, Leu |
| 18 | Ala, Lys, Trp, Arg, His, Leu, Met, Phe |
| 19 | Ala, Lys, D—Glu, Gly, Arg, His, Leu, Ile, Phe, Asn |
| 20 | D—Ile, Ala, Lys, Trp, Leu, Phe, Val, Met |
| 21 | Lys, Pro, Ala, His, Leu, Arg, Ile, Phe |
| 22 | Lys, Ala, D—Asn, Gln, Arg, His |
| 23 | D—Ser, Lys, Ala, Thr, Gly, Leu, Ile, Gln, Asn |

Preferably, the substituted residues are as follows:

| Residue No. | Substituted Residues |
| --- | --- |
| 1 | Lys, Ala |
| 2 | Lys, Ala, D—Ile |
| 3 | Lys, Ala, Trp |
| 4 | D—Lys, Ala |
| 5 | D—Phe, Ala, Lys, Trp |
| 6 | D—Leu, Lys, Ala |
| 7 | Lys, D—His, Ala |
| 8 | Ala, Lys, D—Ser, Trp |
| 9 | Lys, D—Ala, Trp |
| 10 | D—Lys, Lys |
|  | Ala, Trp |
| 11 | D—Lys |
| 12 | D—Phe, Lys, Trp |
| 13 | Ala, Lys, Trp |
| 14 | Ala, D—Lys |
| 15 | Lys, Trp, D—Ala |
| 16 | Ala, Lys, D—Phe |
| 17 | Ala, Lys, D—Val, Trp |
| 18 | Ala, Lys, Trp |
| 19 | Ala, Lys, D—Glu |
| 20 | D—Ile, Ala, Lys, Trp |
| 21 | Lys, Pro, Ala, Leu |
| 22 | Lys, Ala, D—Asn |
| 23 | D—Ser, Lys, Ala, Asn |

It is to be understood that for purposes of the present invention that the methionine residues, whether each such residue is present in its normal position or employed as a substitution residue, may be a normal methionine residue or a methionine sulfoxide residue.

In accordance with a particular embodiment, amino acid residues 16–23 of Magainin I are deleted, and amino acid residues 3, 8 and 10 are substituted with an alanine residue.

In accordance with yet another embodiment, amino acid residue 19 of Magainin I is deleted, and preferably amino acid residues 5, 8, 9 and 16 are each substituted with a lysine residue, amino acid residue 21 is substituted with a leucine residue, and amino acid residues 18 and 23 are substituted with an alanine residue.

In accordance with another embodiment, in carboxy-terminated or amide-terminated (preferably amide-terminated) Magainin I or Magainin II peptide, amino acid residues 17–23 or 16–23 or 15–23 are deleted, and amino acid residues 3, 7, and 8 are each substituted with a lysine residue, and optionally amino acid residue 13 and/or amino acid residue is substituted with an alanine residue. Preferred amide-terminated peptides are as follows:

Gly Ile Lys Lys Phe Leu Lys Lys Ala Gly Lys Phe Gly Lys-NH$_2$ (SEQ ID NO:3)

Gly Ile Lys Lys Phe Leu Lys Lys Ala Gly Lys Phe Gly Lys Ala Phe-NH$_2$ (SEQ ID NO:4)

Gly Ile Lys Lys Phe Leu Lys Lys Ala Lys Lys Phe Gly Lys Ala-NH$_2$ (SEQ ID NO:5)

Gly Ile Lys Lys Phe Leu Lys Lys Ala Lys Lys Phe Ala Lys Ala-NH$_2$ (SEQ ID NO:6) Gly Ile Lys Lys Phe Leu Lys Lys Ala Ala Lys Phe Ala Lys Ala-NH$_2$ (SEQ ID NO:7)

Preliminary studies indicate that the above-mentioned preferred peptides possess low hemolytic activity. In accordance with a further embodiment, amino acid residue 21 of Magainin I may be deleted, and preferably amino acid residues 5,10, 18, and 19 are each substituted with a lysine residue, amino acid residue 7 is substituted with a phenylalanine residue, and amino acid residue 22 is substituted with an alanine residue.

In accordance with another embodiment, in carboxy or amide terminated (preferably amide terminated) Magainin I or Magainin II (preferably Magainin II), amino acid residue 19 is omitted, and at least one of amino acid residues 3, 7, 8, 10, 13, 15, 16, 18 21, 22 or 23 is substituted with another amino acid as follows:

| Residue number | Substituted Residue |
| --- | --- |
| 3 | Leu |
| 7 | Lys |
| 8 | Lys, Ala |
| 10 | Ala, Lys |
| 13 | Trp, Leu, Phe, Ala |
| 15 | Phe |
| 16 | Ala |
| 18 | Lys, Ala, Phe |
| 21 | Lys, Ile, Leu |
| 22 | Lys |
| 23 | Lys, D—Ser, Asn. |

Representative peptides are disclosed in Examples 14 and 21–23.

In a preferred embodiment, the peptide is a Magainin II peptide, and the substitution analogue wherein amino acid 19 is deleted is selected from the class consisting of the following substitution analogues:
Gly Ile Gly Lys Phe Leu His Ser Ala Lys Lys Phe Gly Lys Ala Phe Val Gly Ile Met Lys Ser (SEQ ID NO:8);
Gly Ile Gly Lys Phe Leu His Ser Ala Lys Lys Phe Gly Lys Ala Phe Val Ala Ile Met Lys Ser (SEQ ID NO:9);
Gly Ile Gly Lys Phe Leu His Ser Ala Lys Lys Phe Gly Lys Ala Phe Val Phe Ile Met Asn Ser*, wherein Ser* is D-Serine (SEQ ID NO:10);
Gly Ile Gly Lys Phe Leu His Ser Ala Lys Lys Phe Phe Lys Ala Phe Val Phe Ile Met Asn Ser (SEQ ID NO:11);
Gly Ile Gly Lys Phe Leu Lys Ser Ala Lys Lys Phe Gly Lys Ala Phe Val Phe Ile Met Asn Ser (SEQ ID NO:12);
Gly Ile Gly Lys Phe Leu His Lys Ala Lys Lys Phe Ala Lys Ala Phe Val Phe Ile Met Asn Ser (SEQ ID NO:13);
Gly Ile Gly Lys Phe Leu Lys Ser Ala Lys Lys Phe Ala Lys Ala Phe Val Phe Ile Met Asn Ser (SEQ ID NO:14);
Gly Ile Gly Lys Phe Leu His Lys Ala Lys Lys Phe Ala Lys Ala Phe Val Phe Ile Met Asn Lys (SEQ ID NO:15);
Gly Ile Gly Lys Phe Leu Lys Ser Ala Lys Lys Phe Gly Lys Ala Phe Val Phe Ile Met Lys Lys (SEQ ID NO:16); and
Gly Ile Gly Lys Phe Leu His Ser Ala Lys Lys Phe Gly Lys Ala Phe Val Xaa Ile Met Asn Ser ; wherein Xaa is ε-Fmoc-lysine (SEQ ID NO:17).
Preliminary studies indicate that these preferred analogues possess low hemolytic activity.

In accordance with another embodiment, there are provided derivatives of Magainin I or Magainin II (carboxy- or amide-terminated), preferably Magainin II, wherein a portion of the basic peptide is deleted and at least one of the remaining amino acid residues is substituted as hereinabove described; in particular, amino acid residue 19 is omitted and in addition either amino acid residues 1–4 or 3,5, and 6 are omitted. Preferred peptides are as follows:
Phe Leu His Ser Ala Lys Lys Phe Gly Lys Ala Phe Val Phe Ile Met Asn Ser (SEQ ID NO:18)
Gly Ile Lys His Ser Ala Lys Lys Phe Ala Lys Ala Phe Lys Ala Ile Met Asn Ser (SEQ ID NO:19)
Phe Leu Lys Ser Ala Lys Lys Phe Gly Lys Ala Phe Val Gly Ile Met Asn Ser (SEQ ID NO:20)
Phe Leu Lys Ser Ala Lys Lys Phe Ala Lys Ala Phe Val Gly Ile Met Asn Ser (SEQ ID NO:21)

Applicants have found that when employing the substitution analogues of Magainin I or Magainin II as hereinabove described, such peptides display biological activity equal to or greater than the parent Magainin I or Magainin II peptide. Such peptides are referred to as "successful substitution analogues".

The use of these compounds which comprise a substitution analogue of Magainin I or Magainin II peptide, in accordance with the present invention, is effective as an antibiotic, and can be employed to inhibit, prevent or destroy the growth or proliferation of microbes, such as bacteria, fungi viruses or the like. Similarly, such compounds can be employed as an anti-viral composition to inhibit, prevent or destroy the growth or proliferation of viruses or virally-infected cells.

As used herein, the term "substitution analogue" includes magainin peptides in which at least one amino acid residue of the peptide structure has been substituted with a different amino acid residue, as well as magainin peptides in which, in addition to the above-mentioned substitution(s), also have had at least one of amino acid residues 15–23 omitted from the peptide sequence. The term also includes magainin peptides having D-amino acid or iodinated phenylalanine residues which have been substituted into the peptide sequence.

Such compounds can also be employed as a spermicide to inhibit, prevent or destroy the motility of sperm.

Such compounds can also be employed as anti-tumor agents to inhibit the growth of or destroy tumors.

The compounds have a broad range of potent antibiotic activity against a plurality of microorganisms, including Gram-positive and Gram-negative bacteria, fungi, protozoa and the like. Such compounds can be employed for treating or controlling microbial infection caused by organisms which are sensitive to such compounds.

The compounds can also be used as preservatives or sterilants for materials susceptible to microbial contamination. In vitro activity against bacteria is exemplified hereinafter in Examples 3–27.

In general, a substitution analogue of the Magainin I or Magainin II peptide is administered in a dosage of from about 1 mg to about 500 mg per kilogram of body weight, when administered systemically. When administered topically, the peptide is used in a concentration of from about 0.5% to about 5%.

The compounds comprising the substitution analogues of Magainin I or Magainin II, in accordance with the present invention, can be employed for treating a wide variety of hosts. In accordance with a preferred embodiment, a host can be an animal, and such animal can be a human or non-human animal.

The compounds comprising the substitution analogues of Magainin I or Magainin II can be employed in a wide variety of pharmaceutical compositions in combination with a non-toxic pharmaceutical carrier or vehicle such as a filler, non-toxic buffer, or physiological saline solution. Such pharmaceutical compositions can be used topically or systemically and can be in any suitable form such as a liquid, solid, semi-solid, injectable solutions, tablet, ointment, lotion, paste, capsule or the like. The compounds comprising the substitution analogues of Magainin I or Magainin II can also be used in combination with adjuvants, protease inhibitors, or compatible drugs where such a combination is seen to be desirable or advantageous in controlling infection caused by harmful microorganisms including protozoa, viruses, and the like.

The compounds comprising the substitution analogues of Magainin I or Magainin II of the present invention can be administered to a host; in particular an animal, in an effective antibiotic and/or anti-tumor and/or anti-viral and/or anti-microbial and/or a spermicidal amount.

Magainin I and Magainin II, as well as the substitution analogues of the Magainin I and Magainin II peptides of the present invention, (both amide- and carboxy-terminated Magainin I and Magainin II forms) can be synthesized by any convenient method of peptide synthesis as are well-known to skilled workers. Solid phase synthesis methods are particularly preferred.

The peptides described herein were prepared by the method of simultaneous multiple peptide synthesis (SMPS).

This method is described in detail in Houghten, R. A., "General Method for the Rapid Solid-Phase Synthesis of Large Numbers of Peptides; Specificity of Antigen-Antibody Interaction at the Level of Individual Amino Acids," *Proc. Natl. Acad. Sci. U.S.A.*, Vol. 82, pgs. 5131–5135 (1985), and in Houghten, R. A., et al. "Simultaneous Multiple Peptide Synthesis; The Rapid Preparation of Large Numbers of Discrete Peptides for Biological, Immunological, and Methodological Studies," *Peptide Chemistry*, pgs. 295–298 (1987).

For purposes of the following examples, substitution analogues of Magainin I and Magainin II were prepared wherein various amino acid residues were substituted and/or other amino acid residue(s) were deleted.

For purposes of comparison, a complete Magainin I or Magainin II peptide can also be prepared by the SMPS method. It is also contemplated within the scope of the present invention that substitution analogues which have one or more amino acid residue(s) omitted from the Magainin I or Magainin II structure can also be prepared by the SMPS method.

The invention will now be described with respect to the following examples, however, the scope of the present invention is not intended to be limited thereby.

EXAMPLE 1

Peptide Synthesis

Peptide synthesis of Magainin I and the substitution analogues of Magainin I, was accomplished by using the strategy of simultaneous multiple peptide synthesis. All solvents and reagents were of analytical grade and were used without further purification. Standard N-t-Boc-protected amino acids were employed in the synthesis. The side chain functionalities used were benzyl (Ser, Glu), 2-Cl-Z (Lys) (Z=benzyloxycarbonyl), $N^{im}$-DNP (His), and sulfoxide (Met). Peptide synthesis was performed beginning with 100 mg of either Boc-amino acids-Pam resin to produce C-terminal carboxyl peptide (PAM purchased from Applied Biosystems, substitution 0.56 meq/gm is an amino acyl -4-[oxymethyl] phenylacetic acid derivative of amino polystyrene) or methylbenzhydrylamine (MBHA) resin (substitution—0.65 meq/gm) per resin packet to produce C-terminal amide peptide.

After synthesis, completely protected peptide resins were treated three times with 0.5 M thiophenol in DMF to remove the $N^{im}$-dinitrophenyl group from Histidine. The final Boc-group was removed with TFA to avoid t-butylation of methionyl residues during final HF treatment. Cleavage was performed using the Low-High HF procedure. Tam, et al. *J. Am. Chem. Soc.* Vol. 105, P. 6442 (1983). When methionine is part of the peptide structure, one may elect not to reduce the sulfoxide group on the methionine residue(s), thus resulting in a peptide which includes methionine sulfoxide residue(s). For peptides synthesized on Pam resin, the low-HF was carried out without removing the resin from the packet, using a multiple vessel HF apparatus for 2 hrs. at 0° C. For peptides prepared using MBHA resin, the low HF procedure was performed in a common reaction vessel for 2 hrs. at 0° C. For Pam resin peptides, the low-HF mixture was evacuated from the 24 individual reaction vessels by a water aspirator followed by a mechanical pump. The low-HF reaction vessel containing the bags with MBHA resin was emptied of the low-HF mixture by pouring off the liquid into a waste container. The bags were washed immediately with cold ether followed by alternating washes of $CH_2Cl_2$, DMF, $CH_2Cl_2$, IPA, $CH_2Cl_2$. The packets were then dried and put into individual tubes of the 24 vessel HF apparatus with 0.7 ml of anisole as scavenger. The high-HF was performed by condensing dry hydrogen fluoride at −70° C. The reaction took place at −10° C. for 1 h. and −5° C.–0° C. for the last 30 min. HF was evaporated using a strong flow of nitrogen. Finally, residual carbonium ion scavengers were removed by washing with dry ether.

The crude peptides were subsequently extracted with 10% acetic acid and subjected to RP-HPLC on an analytical reversed phase column (Vidac ODS 25 cm×4.6 mm), using a Beckman-Altek model 421 HPLC system and two model 110A pumps. The solvent system was composed of buffer A, 0.05% $TFA/H_2O$, and buffer B, 0.05% $TFA/CH_3CN$ with a flow rate of 1.0 ml/min. The peptides were detected at 215 nm using a Hitachi 100-20 spectrophotometer.

Purification of the peptides was accomplished by reverse-phase HPLC on a Vidac $C_{18}$ (22 mm×25 cm), 10 μm packing column with an eluting gradient composed of $CH_3CN$ and 0.05% TFA. Amino acid analysis was carried out on a Beckman 6300 analyzer following hydrolysis of the peptides in constant (boiling) 6 N HCl at 110° C. for 24 hr., and such analysis was within +10% of theory.

EXAMPLE 2

Antimicrobial Assays

Antimicrobial assays (for Examples 3 to 27) were carried out in 96-well tissue culture plates. Each well was incubated with a given microorganism (*Escherichia coli, Staphylococcus epidermidis, Staphylococcus aureus*, or *Pseudomonas aeruginosa*) suspended in LB medium (Examples 3–17), or TSB medium (Examples 18–27). Upon the addition of Magainin I or its substitution analogues, (dissolved in 1×PBS, pH 7.0) each well contained a final cell density of $1.0 \times 10^6$ colony forming units (CFU)/ml. The final peptide concentrations used were 100 μg/ml., 75.0 μg/ml, 50.0 μg/ml, 25 μg/ml, 12.5 μg/ml, 10 μg/ml, 5μg/ml, 2.5 μg/ml, and 1.25 μg/ml.

Addition of peptides to the wells was defined as time zero. At six hours, the plates were placed in a Titertek Multiskan apparatus and the $O.D._{620}$ determined. The plates as well as the initial innoculum were incubated at 37° C.

Five wells per plate contained media alone, while five others contained medium plus cells. These controls were used to eliminate the possibility of media contamination while providing a measure of uninhibited growth of the microorganisms.

The degree of peptide activity was determined by comparing the substitution analogues with uninhibited growth of the control cells over a six-hour period. The effective growth inhibition of the substitution analogues is listed in the examples and tables below.

EXAMPLE 3

Magainin I Analogues with Alanine Substitutions

Magainin I and analogues wherein an alanine residue was substituted for various amino acid residues of Magainin I were prepared as hereinabove described in Example 1 and tested for % effective growth inhibition of *E. coli* at a concentration given in μg/ml as hereinanbove described in Example 2. The % effective growth inhibition at a concentration in μg/ml for the alanine-substituted Magainin I analogues is listed below in Table I. As used herein, the heading "Amino Acid Residue Substituted" refers to the number of the amino acid residue in the peptide which is substituted with a desired amino acid residue. All other residues in the peptide remain the same as that of the normal peptide sequence. For purposes of explanation of the term "% effective growth inhibition," a value of "100 at 25", for example, indicates 100% effective growth inhibition at a concentration of 25 μg/ml.

TABLE 1

Alanine-Substituted Magainin I Analogues

| Amino Acid Residue Substituted | % Effective Growth Inhibition Concentration in μg/ml |
|---|---|
| None (Magainin I) | 100 at 25 |
| 23 | 100 at 10 |
| 22 | 100 at 50 |
| 21 | 100 at 50 |
| 20 | 100 at 50 |
| 19 | 100 at 5 |
| 18 | 100 at 25 |
| 17 | 100 at 75 |
| 16 | 100 at 25 |
| 14 | 100 at 100 |
| 13 | 100 at 25 |
| 12 | 100 at 50 |
| 11 | 0 at 100 |
| 10 | 100 at 25 |
| 8 | 100 at 5 |
| 7 | 100 at 75 |
| 6 | 0 at 100 |
| 5 | 0 at 100 |
| 4 | 0 at 100 |
| 3 | 100 at 75 |
| 2 | 100 at 100 |
| 1 | 100 at 100 |

Magainin I analogues were also prepared wherein amino acid residues 19, 16, or 8, respectively, were substituted with alanine residues, and such substitution analogues were tested for % effective growth inhibition of *S. epidermidis* and/or *S. aureus* as compared to Magainin I without any substitutions. Magainin I had a % effective growth inhibition of *S.epidermidis* of 100% at 25 μg/ml and of *S.aureus* of 80% at 100 μg/ml. The % effective growth inhibition of *S. epidermidis* for the substitution analogue of Magainin I wherein amino acid residue 19 was substituted with alanine was 100% at 25 μg/ml, and for the substitution analogue of Magainin I wherein amino acid residue 16 was substituted with an alanine residue was 75% at 100 μg/ml. The % effective growth inhibition of *S. aureus* for the substitution analogue of Magainin I wherein amino acid residue 19 was substituted with alanine was 100% at 25 μg/ml, and for the substitution analogue of Magainin I wherein amino acid residue 8 was substituted with alanine was 100% at 50 μg/ml.

EXAMPLE 4

Magainin I Analogues with Proline Substitutions

Magainin I analogues wherein a proline residue was substituted for various amino acid residues of Magainin I were prepared and tested as hereinabove described for % effective growth inhibition of *E. coli* at a concentration given in μg/ml. The % effective growth inhibition for each of the proline-substituted analogues of Magainin I is listed below in Table II.

TABLE II

Proline-Substituted Magainin I Analogues

| Amino Acid Residue Substituted | % Effective Growth Inhibition Concentration in μg/ml |
|---|---|
| 22 | 0 at 100 |
| 21 | 100 at 25 |
| 20 | 100 at 100 |
| 19 | 100 at 50 |
| 18 | 100 at 75 |

TABLE II-continued

Proline-Substituted Magainin I Analogues

| Amino Acid Residue Substituted | % Effective Growth Inhibition Concentration in μg/ml |
|---|---|
| 17 | 0 at 100 |
| 16 | 0 at 100 |
| 15 | 50 at 100 |
| 14 | 0 at 100 |
| 13 | 100 at 100 |
| 12 | 0 at 100 |
| 11 | 0 at 100 |
| 10 | 0 at 100 |
| 9 | 100 at 100 |
| 8 | 100 at 75 |
| 7 | 0 at 100 |
| 6 | 0 at 100 |
| 4 | 0 at 100 |
| 3 | 100 at 75 |
| 2 | 0 at 100 |
| 1 | 100 at 100 |

EXAMPLE 5

Lysine-Substituted Magainin I Analogues

Magainin I analogues wherein a lysine residue was substituted for various amino acid residues of Magainin I were prepared and tested as hereinabove described for % effective growth inhibition of *E.coli* at a concentration given in μg/ml. The % effective growth inhibition of each lysine-substituted analogue of Magainin I is given below in Table III.

TABLE III

Lysine-Substituted Analogues of Magainin I

| Amino Acid Residue Substituted | % Effective Growth Inhibition Concentration in μg/ml |
|---|---|
| 23 | 100 at 5 |
| 21 | 100 at 25 |
| 20 | 100 at 25 |
| 19 | 100 at 2.5 |
| 18 | 100 at 25 |
| 17 | 100 at 100 |
| 16 | 0 at 100 |
| 15 | 100 at 50 |
| 13 | 100 at 50 |
| 12 | 100 at 100 |
| 10 | 100 at 25 |
| 9 | 100 at 100 |
| 8 | 100 at 5 |
| 7 | 100 at 5 |
| 6 | 0 at 100 |
| 5 | 0 at 100 |
| 3 | 100 at 25 |
| 2 | 100 at 100 |
| 1 | 100 at 50 |

Magainin I analogues wherein amino acid residues 23, 19, 8, or 7, respectively, were substituted with a lysine residue were tested for % effective growth inhibition of *S. epidermidis* and/or *S. aureus*. The substitution analogue of Magainin I wherein amino acid residue 23 was substituted with a lysine residue had a % effective growth inhibition of *S. aureus* of 30% at 100 μg/ml. The substitution analogue of Magainin I wherein amino acid residue 19 was substituted with a lysine residue had a % effective growth inhibition of *S. epidermidis* of 100% at 25 μg/ml, and of *S. aureus* of 50% at 100 μg/ml. The substitution analogue of Magainin I wherein amino acid residue 8 was substituted with a lysine residue had a % effective growth inhibition of *S. aureus* of 70% at 100 μg/ml. The substitution analogue of Magainin I wherein amino acid residue 7 was substituted with a lysine residue had a % effective growth inhibition of *S. epidermidis* of 100% at 25 μg/ml, and of *S. aureus* of 100% at 50 μg/ml.

EXAMPLE 6

Glutamic Acid-Substituted Magainin I Analogues

Magainin I analogues wherein a glutamic acid residue was substituted for various amino acid residues of Magainin I were prepared and tested for % effective growth inhibition of *E.coli* according to the methods hereinabove described. The % effective growth inhibition for each glutamic acid-substituted Magainin I analogue is described below in Table IV.

TABLE IV

Glutamic Acid-Substituted Analogues of Magainin I

| Amino Acid Residue Substituted | % Effective Growth Inhibition Concentration in μg/ml |
|---|---|
| 22 | 0 at 100 |
| 21 | 100 at 75 |
| 20 | 0 at 100 |
| 18 | 100 at 75 |
| 17 | 0 at 100 |
| 16 | 0 at 100 |
| 15 | 0 at 100 |
| 14 | 0 at 100 |
| 13 | 0 at 100 |
| 12 | 0 at 100 |
| 11 | 0 at 100 |
| 10 | 100 at 75 |
| 9 | 0 at 100 |
| 8 | 100 at 75 |
| 7 | 32 at 100 |
| 3 | 0 at 100 |

EXAMPLE 7

Maqainin I Peptides Containing D-amino Acid Residues

Magainin I peptides were synthesized wherein in each peptide one of amino acid residues 23, 19, 17, 16, 14, 4, or 2, respectively, is substituted with a D-amino acid residue. Each of these Magainin I peptide analogues was then tested as hereinabove described for % effective growth inhibition of *E.coli* in μg/ml. The % effective growth inhibition for each of the D-amino acid residue-subsituted analogues of Magainin I is listed below in Table V.

TABLE V

D-amino acid residue-substituted Magainin I Analogues

| Amino Acid Residue Substituted | % Effective Growth Inhibition Concentration in μg/ml |
|---|---|
| 23 | 100 at 10 |
| 19 | 100 at 25 |
| 17 | 100 at 50 |
| 16 | 100 at 50 |
| 14 | 100 at 50 |
| 4 | 100 at 25 |
| 2 | 100 at 25 |

EXAMPLE 8

In this example, a substitution analogue of Magainin I was prepared wherein amino acid residue 19, (E, or glutamic acid) was deleted, and amino acid residues 5, 8, 9, and 16 are each substituted with a lysine residue, amino acid residue 21 is substituted with a leucine residue, and amino acid residues 18 and 23 are each substituted with an alanine residue. The substitution analogue had the following structure:
Gly Ile Gly Lys Lys Leu His Lys Lys Gly Lys Phe Gly Lys Phe Lys Gly Ala Ile Leu Lys Ala (SEQ ID NO:22)

The % effective growth inhibition of *E.coli* for this peptide was tested and found to be 100% at 5 μg/ml.

EXAMPLE 9

In this example, a substitution analogue of Magainin I was prepared wherein amino acid 21 was deleted and amino acid residues 5, 10, 18, and 19 were each substituted with a lysine residue, amino acid residue 7 was substituted with a phenylalanine residue, and amino acid 22 was substituted with an alanine residue. The peptide had the following structure:
Gly Ile Gly Lys Lys Leu Phe Ser Ala Lys Lys Phe Gly Lys Ala Phe Val Lys Lys Ile Ala Ser (SEQ ID NO:23)

The % effective growth inhibition of *E.coli* for this peptide was tested and found to be 100% at 2.5 μg/ml.

EXAMPLE 10

Magainin I and Magainin II peptides were prepared wherein phenylalanine residues 5 and 12 in each peptide were iodinated. The % effective growth inhibition of *E.coli* for each peptide, containing the iodinated phenylalanine residues, was tested. For the Magainin I peptide, the % effective growth inhibition was 100% at 10 μg/ml. For the Magainin II peptide, the % effective growth inhibition was 100% at 5 μg/ml.

EXAMPLE 11

Tryptophan (Formyl Group Removed)-Substituted Analoaues of Magainin I

Magainin I analogues were prepared wherein a tryptophan residue was substituted for various amino acid residues of Magainin I. The tryptophan had the formyl group removed, thus resulting in the substitution of unprotected tryptophan residues into the Magainin I analogues. % effective growth inhibition of *E.coli* and *S. epidermidis* was tested for these analogues. % effective growth inhibition of *E. coli* and *S. epidermidis* in μg/ml is listed below in Table VI.

TABLE VI

Tryptophan (Formyl Group Removed) - Substituted Analogues of Magainin I

| Amino Acid Residue Substituted | % Effective Growth Inhibition Concentration in uq/ml | |
|---|---|---|
| | *E. coli* | *S. epidermidis* |
| 1 | 100 at 50 | 80 at 75 |
| 3 | 100 at 25 | 100 at 50 |
| 4 | 90 at 100 | 0 at 100 |
| 5 | 100 at 25 | 80 at 100 |
| 6 | 100 at 50 | 50 at 75 |
| 8 | 100 at 100 | 100 at 50 |
| 9 | 100 at 25 | 40 at 100 |
| 10 | 100 at 25 | 100 at 50 |
| 11 | 0 at 100 | 0 at 100 |
| 12 | 100 at 25 | 0 at 100 |
| 13 | 100 at 25 | 100 at 50 |
| 14 | N/A | 0 at 100 |
| 15 | 96 at 10 | 90 at 100 |
| 16 | 95 at 50 | 0 at 100 |
| 17 | 100 at 25 | 100 at 100 |
| 18 | 93 at 25 | 90 at 100 |

TABLE VI-continued

Tryptophan (Formyl Group Removed) -
Substituted Analogues of Magainin I

| Amino Acid Residue Substituted | % Effective Growth Inhibition Concentration in ug/ml | |
|---|---|---|
| | E. coli | S. epidermidis |
| 19 | 100 at 10 | 100 at 75 |
| 20 | 90 at 25 | 30 at 100 |
| 21 | 100 at 50 | 0 at 100 |
| 22 | 40 at 75 | 0 at 100 |

EXAMPLE 12

Tryptophan (Containing Formyl Group)-Substituted Magainin I Analogues

Magainin I analogues were prepared wherein a tryptophan residue was substituted for various amino acid residues of Magainin I, as in Example 11, except that in this example, the formyl group remained on the tryptophan residue thus resulting in the substitution of protected tryptophan residues into the Magainin I analogues. % effective growth inhibition of E.coli and S. epidermidis was tested for each of these analogues. % effective growth inhibition of E.coli and S. epidermidis in µg/ml is listed below in Table VII.

TABLE VII

Tryptophan (containing formyl group) -
Substituted Analogues of Magainin I

| Amino Acid Residue Substituted | % Effective Growth Inhibition Concentration in µg/ml | |
|---|---|---|
| | E. coli | S. epidermidis |
| 1 | 100 at 50 | 100 at 75 |
| 3 | 100 at 50 | 100 at 75 |
| 4 | 70 at 100 | 0 at 100 |
| 5 | 100 at 50 | 100 at 100 |

TABLE VII-continued

Tryptophan (containing formyl group) -
Substituted Analogues of Magainin I

| Amino Acid Residue Substituted | % Effective Growth Inhibition Concentration in µg/ml | |
|---|---|---|
| | E. coli | S. epidermidis |
| 6 | 100 at 50 | 100 at 100 |
| 7 | 100 at 75 | 90 at 100 |
| 8 | 100 at 25 | 100 at 75 |
| 9 | 100 at 50 | 44 at 100 |
| 10 | 100 at 25 | 100 at 75 |
| 11 | 0 at 100 | 0 at 100 |
| 12 | 100 at 25 | 90 at 75 |
| 13 | 100 at 10 | 100 at 50 |
| 14 | 0 at 100 | 0 at 100 |
| 15 | 100 at 10 | 100 at 75 |
| 16 | 100 at 50 | 0 at 100 |
| 17 | 100 at 50 | 100 at 75 |
| 18 | 100 at 25 | 63 at 100 |
| 19 | 100 at 75 | N/A |
| 20 | 100 at 25 | 55 at 100 |
| 21 | 92 at 50 | 36 at 100 |
| 22 | 80 at 75 | 0 at 100 |

EXAMPLE 23

Multiple-Substitution Analogues of MAGAININ I with Lysine and/or Alanine Residues Analogues of Magainin I were prepared wherein amino acid residues 3, 8, 9, 16, 19, and/or 23 were substituted with alanine (A) or lysine (K) residues. % effective growth inhibition of E. coli, S. epidermidis, and/or S. aureus was tested for each substitution analogue. The structure of each synthesized substitution analogue as well as the % effective growth inhibition of E. coli, S. epidermidis, and S. aureus in µg/ml are given below in Table VIII.

TABLE VIII

| PEPTIDE STRUCTURE | % EFFECTIVE GROWTH INHIBITION CONCENTRATION IN µG/ML | | |
|---|---|---|---|
| | E. COLI | S. EPIDERMIS | S. AUREUS |
| GIAKFLHAAGKFGKAAVGAIMKA (SEQ ID NO:24) | 90 at 2.5 | N/A | 100 at 75 |
| GIAKFLHAAGKFGKAAVGAIMKK (SEQ ID NO:25) | 100 at 2.5 | 100 at 25 | 74 at 100 |
| GIAKFLHAAGKFGKAAVGKIMKA (SEQ ID NO:26) | 100 at 2.5 | 100 at 25 | 100 at 75 |
| GIAKFLHAKGKFGKAAVGAIMKA (SEQ ID NO:27) | 90 at 10 | N/A | 0 at 100 |
| GIAKFLHKAGKFGKAAVGAIMKA (SEQ ID NO:28) | 100 at 2.5 | 100 at 25 | 100 at 50 |
| GIKKFLHAAGKFGKAAVGAIMKA (SEQ ID NO:29) | 100 at 2.5 | 100 at 25 | 100 at 25 |
| GIKKFLHKKGKFGKAAVGKIMKK (SEQ ID NO:30) | 96 at 2.5 | N/A | 0 at 100 |

EXAMPLE 14

Magainin I Analgaues with Glutamic Acid Omissions and Alanine or Lysine Substitutions Magainin I analogues were prepared wherein amino acid residue 19 (E, or glutamic acid) was deleted, and either alanine or lysine was substituted for one of the remaining amino acid residues in the peptide. Alanine was substituted for either residue 16, 10 or 8, or lysine was substituted for either residue 18, 8, or 7. Each of these substitution analogues was tested for % effective growth inhibition of E. coli, S. epidermidis, and/or S. aureus. The structures of each peptide and the % effective growth inhibition of E. coli, S. epidermidis, or S. aureus in μg/ml are listed below in Table IX.

TABLE IX

% EFFECTIVE GROWTH INHIBITION CONCENTRATION IN μG/ML

| PEPTIDE STRUCTURE | E. COLI | S. EPI-DERMIS | S. AUREUS |
|---|---|---|---|
| GIGKFLHSAGKFGKAAVGIMKS (SEQ ID NO:31) | 100 at 25 | 100 at 100 | N/A |
| GIGKFLHSAAKFGKAFVGIMKS (SEQ ID NO:32) | 100 at 2.5 | N/A | 100 at 50 |
| GIGKFILHAAGKFGKAFVGIMKS (SEQ ID NO:33) | 100 at 2.5 | 100 at 25 | 100 at 50 |
| GIGKFLHSAGKFGKAFVKIMKS (SEQ ID NO:34) | 100 at 2.5 | 100 at 10 | N/A |
| GIGKFLHKAGKFGKAFVGIMKS (SEQ ID NO:35) | 109 at 2.5 | 84 at 10 | N/A |
| GIGKFLKSAGKFGKAFVGIMKS (SEQ ID NO:36) | 100 at 2.5 | 97 at 12.5 | N/A |

EXAMPLE 15

Magainin I substitution analogues were prepared in which, in one analogue, each of amino acid residues 8, 19, and 23 was substituted with lysine, and, in another analogue each of amino acid residues 7, 8, 19, and 23 was substituted with lysine. % effective growth inhibition of E. coli and S. epidermidis in μg/ml was then measured. For the analogue in which amino acid residues 8, 19, and 23 were substituted with lysine, the % effective growth inhibition of E. coli was 100% at 2.5 μg/ml and of S. epidermidis was 100% at 12.5 μg/ml, for the analogue in which amino acid residues 7, 8, 19, 23 were substituted with lysine, the % effective growth inhibition of E. coli was 100% at 1.25 μg/ml and the % effective growth inhibition of S. epidermidis was 100% at 5 μg/ml.

EXAMPLE 16

In this example, an analogue of Magainin I was prepared wherein amino acid residues 16 through 23 were deleted and residues 3, 7, and 8 were substituted with lysine residues. The resulting peptide had the following structure:
Gly Ile Lys Lys Phe Leu Lys Lys Ala Gly Lys Phe Gly Lys Ala (SEQ ID NO:37)

The peptide was then tested for % effective growth inhibition of E. coli. The % effective growth inhibition of E. coli for this peptide was found to be 100% at 5 μg/ml.

EXAMPLE 17

In this example, an analogue of Magainin I was prepared wherein amino acid residues 16 through 23 were deleted and amino acid residues 3, 8, and 10 were substituted with an alanine residue. The resulting peptide has the following structure:
Gly Ile Ala Lys Phe Leu His Ala Ala Ala Lys Phe Gly Lys Ala (SEQ ID NO:38)

The peptide was tested for % effective growth inhibition of E. coli. The % effective growth inhibition of E. coli for this peptide was found to be 100% at 25 μg/ml.

EXAMPLE 18

Magainin II Analogues with Alanine Substitutions

Magainin II and analogues wherein an alanine residue was substituetd for various amino acid residues of Magainin II were prepared as hereinabove described in Example 1 and tested for % effective growth inhibition of E-Coli, P.aeruainosa, and S. epidermidis as hereinabove described in Example 2. The % effective growth inhibition at a concentration in μg/ml for the alanine-substituted Magainin II analogues is listed below in Table X.

TABLE X

Alanine - Substituted Magainin II Analogues
% Effective Growth Inhibition Concentration
μg/ml

| Amino Acid Residue Substituted | E. Coli | P. aeruginosa | S. epidermidis |
|---|---|---|---|
| None (Magainin II) | 100 at 10 | 100 at 50 | 100 at 25 |
| 23 | 100 at 10 | 100 at >50 | 100 at 25 |
| 22 | 100 at 25 | 100 at 25 | 100 at 25 |
| 21 | 100 at 25 | 100 at 25 | 100 at 25 |
| 20 | 100 at 50 | 100 at 25 | 100 at 50 |
| 19 | 100 at 5 | 100 at 10 | 100 at 5 |
| 18 | 100 at 10 | 100 at 5 | 100 at 25 |
| 16 | 100 at 25 | 100 at 25 | 100 at >50 |
| 14 | 100 at 25 | 100 at 25 | 100 at >50 |
| 13 | 100 at 5 | 100 at 10 | 100 at 25 |
| 12 | 100 at 25 | 100 at >50 | 100 at >50 |
| 11 | 100 at 25 | 100 at >50 | 100 at >50 |
| 10 | 100 at 10 | 100 at 25 | 100 at 25 |
| 8 | 100 at 10 | 100 at 10 | 100 at 10 |
| 7 | 100 at 25 | 100 at 25 | 100 at 25 |
| 6 | 100 at 50 | 100 at 50 | 100 at >50 |
| 5 | 100 at 50 | 100 at 50 | 100 at >50 |
| 4 | 100 at 25 | 100 at 50 | 100 at 50 |
| 3 | 100 at 25 | 100 at 25 | 100 at 25 |
| 2 | 100 at 25 | 100 at 50 | 100 at 50 |
| 1 | 100 at 25 | 100 at 25 | 100 at 50 |

EXAMPLE 19

Magainin II Analogues with Lysine Substiutions

Magainin II analogues wherein a lysine residue was substituted for various amino acid residues of Magainin II where prepared and tested as hereinabove described for % effective growth inhibition of E. Coli, P. aeruginosa, and S. epidermidis at concentrations given in μg/ml. The % effective growth inhibition for each of the Lysine-substituted analogue of Magainin II is listed below in Table XI.

TABLE XI

Lysine-Substituted Magainin II Analogues
% Effective Growth Inhibition Concentration in μg/ml

| Amino Acid Residue Substituted | E. Coli | P. aeruginosa | S. epidermidis |
|---|---|---|---|
| 23 | 100 at 25 | 100 at 50 | 100 at 50 |
| 22 | 100 at 25 | 100 at 25 | 100 at 10 |
| 21 | 100 at 10 | 100 at 25 | 100 at 25 |
| 20 | 100 at 25 | 100 at 25 | 100 at 50 |
| 19 | 100 at 5 | 100 at 10 | 100 at 5 |
| 18 | 100 at 2.5 | 100 at 5 | 100 at 5 |
| 17 | 100 at 25 | 100 at 25 | 100 at 25 |
| 16 | 100 at 25 | 100 at 25 | 100 at 50 |
| 15 | 100 at 5 | 100 at 10 | 100 at 10 |
| 13 | 100 at 5 | 100 at 25 | 100 at 25 |
| 12 | 100 at 10 | 100 at 25 | 100 at 25 |
| 9 | 100 at 25 | 100 at 25 | 100 at 25 |
| 8 | 100 at 5 | 100 at 5 | 100 at 25 |
| 7 | 100 at 5 | 100 at 5 | 100 at 25 |
| 6 | 100 at 10 | 100 at 25 | 100 at 50 |
| 5 | 100 at 25 | 100 at 50 | 100 at 50 |

TABLE XI-continued

Lysine-Substituted Magainin II Analogues
% Effective Growth Inhibition Concentration in μg/ml

| Amino Acid Residue Substituted | E. Coli | P. aeruginosa | S. epidermidis |
|---|---|---|---|
| 3 | 100 at 5 | 100 at 25 | 100 at 10 |
| 2 | 100 at 10 | 100 at 10 | 100 at 25 |
| 1 | 100 at 5 | 100 at 10 | 100 at 25 |

EXAMPLE 20

Magainin II Peptides Containing D-Amino Acid Residues

Magainin II peptides were synthesized wherein various amino acid residues were substituted with a D-amino acid residue, whose structure corresponded to to that of the residue originally present in Magainin II. Each of these Magainin II peptide analogues was then tested as hereinabove described for % effective growth inhibition of E. Coli, P. aeruainosa, and S. epidermidis in μg/ml. The % effective growth inhibition for each of the D-Amino acid residue substituted analogues of Magainin II is listed below in Table XII.

TABLE XII

D-Amino Acid Residue - Substituted Magainin II Analogues
% Effective Growth Inhibition Concentration in μg/ml

| Amino Acid Residue Substituted | E. Coli | P. aeruginosa | S. epidermidis |
|---|---|---|---|
| 23 | 100 at 5 | 100 at 10 | 100 at 25 |
| 22 | 100 at 10 | 100 at 10 | 100 at 25 |
| 20 | 100 at 25 | 100 at 25 | 100 at 50 |
| 19 | 100 at 25 | 100 at 25 | 100 at 25 |
| 17 | 100 at 25 | 100 at 25 | 100 at 50 |
| 16 | 100 at 25 | 100 at 25 | 100 at 25 |
| 15 | 100 at 25 | 100 at 25 | 100 at >50 |
| 14 | 100 at 25 | 100 at >25 | 100 at >50 |
| 12 | — | 100 at 25 | 100 at 50 |
| 11 | 100 at 25 | 100 at 25 | 100 at 25 |
| 10 | 100 at 25 | 100 at 25 | 100 at 25 |
| 9 | 100 at 25 | 100 at 25 | 100 at 25 |
| 8 | 100 at 25 | 100 at 25 | 100 at 25 |
| 7 | 100 at 10 | 100 at 25 | 100 at 25 |
| 6 | 100 at 25 | 100 at 25 | 100 at 50 |
| 5 | 100 at 25 | 100 at 25 | 100 at 50 |
| 4 | 100 at 25 | 100 at 25 | 100 at 50 |
| 2 | 100 at 25 | 100 at 25 | 100 at 50 |

EXAMPLE 21

Magainin II Analogues with Glutamic Acid Deletions

In this example, analogues of Magainin II were synthesized, said analogues having amino acid residue 19 (glutamic acid) deleted from the peptide structure, and wherein one or more of the other amino acid residues was substituted with an amino acid residue different from the normal amino acid residue. Analogues of the following structures were then synthesized according to the method described in Example 1.

| Analogue | Structure |
|---|---|
| 1 | Gly Ile Gly Lys Phe Leu His Ser Ala Lys Lys Phe Trp Lys Ala Phe Val Gly Ile Met Asn Ser (SEQ ID NO: 39) |
| 2 | Gly Ile Gly Lys Phe Leu His Ser Ala Lys Lys Phe Leu Lys Ala Phe Val Gly Ile Leu Asn Ser (SEQ ID NO: 40) |
| 3 | Gly Ile Leu Lys Phe Leu His Ser Ala Lys Lys Phe Leu Lys Ala Phe Val Gly Ile Leu Asn Ser (SEQ ID NO: 41) |
| 4 | Gly Ile Leu Lys Phe Leu His Ser Ala Lys Lys Phe Phe Lys Ala Phe Val Lys Ile Leu Asn Ser (SEQ ID NO: 42) |
| 5 | Gly Ile Gly Lys Phe Leu His Ser Ala Lys Lys Phe Phe Lys Ala Phe Val Phe Ile Leu Asn Ser (SEQ ID NO: 43) |
| 6 | Gly Ile Gly Lys Phe Leu His Ser Ala Lys Lys Phe Gly Lys Ala Phe Val Gly Ile Met Lys Ser (SEQ ID NO: 8) |
| 7 | Gly Ile Gly Lys Phe Leu His Ser Ala Lys Lys Phe Gly Lys Ala Phe Val Ala Ile Met Lys Ser (SEQ ID NO: 9) |
| 8 | Gly Ile Gly Lys Phe Leu His Ser Ala Lys Lys Phe Gly Lys Ala Phe Val Phe Ile Met Asn Ser* (SEQ ID NO: 10) |
| 9 | Gly Ile Gly Lys Phe Leu His Ser Ala Lys Lys Phe Ala Lys Ala Phe Val Phe Ile Met Asn Ser (SEQ ID NO: 44) |
| 10 | Gly Ile Gly Lys Phe Leu His Ser Ala Lys Lys Phe Phe Lys Ala Phe Val Phe Ile Met Asn Ser (SEQ ID NO: 11) |
| 11 | Gly Ile Gly Lys Phe Leu Lys Ser Ala Lys Lys Phe Gly Lys Ala Phe Val Phe Ile Met Asn Ser (SEQ ID NO: 12) |
| 12 | Gly Ile Gly Lys Phe Leu His Lys Ala Lys Lys Phe Ala Lys Ala Phe Val Phe Ile Met Asn Ser (SEQ ID NO: 13) |
| 13 | Gly Ile Gly Lys Phe Leu Lys Ser Ala Lys Lys Phe Ala Lys Ala Phe Val Phe Ile Met Asn Ser (SEQ ID NO: 14) |
| 14 | Gly Ile Gly Lys Phe Leu His Lys Ala Lys Lys Phe Phe Lys Ala Phe Val Phe Ile Met Asn Ser (SEQ ID NO: 45) |
| 15 | Gly Ile Gly Lys Phe Leu Lys Ser Ala Lys Lys Phe Phe Lys Ala Phe Val Phe Ile Met Asn Ser (SEQ ID NO: 46) |
| 16 | Gly Ile Gly Lys Phe Leu His Lys Ala Lys Lys Phe Ala Lys Ala Phe Val Phe Ile Met Asn Lys (SEQ ID NO: 15) |
| 17 | Gly Ile Gly Lys Phe Leu Lys Ser Ala Lys Lys Phe Ala Lys Phe Phe Val Phe Ile Met Asn Lys (SEQ ID NO: 47) |
| 18 | Gly Ile Gly Lys Phe Leu Lys Lys Ala Lys Lys Phe Gly Lys Ala Phe Val Phe Ile Met Lys Lys (SEQ ID NO: 16) |
| 19 | Gly Ile Gly Lys Phe Leu His Ser Ala Lys Lys Phe Gly Lys Ala Phe Val X** Ile Met Asn Ser (SEQ ID NO: 17) |
| 20 | Gly Ile Gly Lys Phe Leu His Ser Ala Lys Lys Phe Gly Lys Ala Phe Val Lys Ile Met Asn Ser (SEQ ID NO: 48) |
| 21 | Gly Ile Gly Lys Phe Leu His Lys Ala Lys Lys Phe Gly Lys Ala Phe Val Lys Ile Met Asn Ser (SEQ ID NO: 49) |

\* = D-Serine
\*\* -ε-Fmoc-lysine

Each of the peptides was then tested as hereinabove described for % effective growth inhibition of E. coli, P.aeruginosa, and S.epidermidis in μg/ml. The % effective growth inhibition of each of these analogues is given in Table XIII below.

TABLE XIII

| | % Effective Growth Inhibition, Concentration in µg/ml | | |
|---|---|---|---|
| Analogue | E. Coli | P. aeruginosa | S. epidermidis |
| 1 | 100 at 5 | 100 at 5 | 100 at 5 |
| 2 | 100 at 2.5 | 100 at 2.5 | 100 at 5 |
| 3 | 100 at 2.5 | 100 at 2.5 | 100 at 5 |
| 4 | 100 at 2.5 | 100 at 2.5 | 100 at 5 |
| 5 | 100 at 10 | 100 at 5 | 100 at 5 |
| 6 | 100 at 5 | 100 at 10 | 100 at 25 |
| 7 | 100 at 2.5 | 100 at 5 | 100 at 5 |
| 8 | 100 at 5 | 100 at 5 | 100 at 5 |
| 9 | 100 at 5 | 100 at 2.5 | 100 at 5 |
| 10 | 100 at 5 | 100 at 10 | 100 at 5 |
| 11 | 100 at 5 | 100 at 5 | 100 at 5 |
| 12 | 100 at 1.25 | 100 at 2.5 | 100 at 1.25 |
| 13 | 100 at 2.5 | 100 at 1.25 | 100 at 2.5 |
| 14 | 100 at 10 | 100 at 2.5 | 100 at 2.5 |
| 15 | 100 at 5 | 100 at 5 | 100 at 1.25 |
| 16 | 100 at 1.25 | 100 at 1.25 | 100 at 1.25 |
| 17 | 100 at 1.25 | 100 at 5 | 100 at 2.5 |
| 18 | 100 at 2.5 | 100 at 2.5 | 100 at 2.5 |
| 19 | 100 at 10 | 100 at 10 | 100 at 5 |
| 20 | 100 at 1.25 | 100 at 2.5 | 100 at 1.25 |
| 21 | 100 at 1.25 | 100 at 5 | 100 at 2.5 |

EXAMPLE 22

Amide (NH₂)-terminated Magainin II analogues wherein amino acid residue 19 (glutamic acid) was deleted, and other amino acid residues were substitued. The analogues are as follows:

| Analogue 1 | Gly Ile Gly Lys Phe Leu Lys Lys Ala Lys Lys Phe Ala Lys Ala Phe Val Lys Ile Ile Asn Asn—NH₂ (SEQ ID NO: 50) |
|---|---|
| Analogue 2 | Gly Ile Gly Lys Phe Leu Lys Lys Ala Ala Lys Phe Ala Lys Ala Phe Val Lys Ile Ile Asn Asn—NH₂ (SEQ ID NO: 51) |

The analogues were then tested as hereinabove described for % effective growth inhibition of E. coli, P.aeruginosa, and S.epidermidis Analogue 1 had % effective growth inhibitions of 100% at 1.25 µg/ml for E. Coli, 100% at 2.5 µg/ml for P.aeruginosa, and 100% at 1.25 µg/ml for S.epidermidis Analogue 2 had % effective growth inhibitions of 100% at 1.25 µg/ml for P. aeruginosa and 100% at 1.25 µg/ml for S.epidermidis.

EXAMPLE 23

Amide (NH2)-terminated analogues, which by virtue of their structures, may be analogues of Magainin I or Magainin II, were synthesized wherein amino acid residue 19 (glutamic acid) was deleted, and other amino acid residues were substituted. The analogues are as follows:

| Analogue 1 | Gly Ile Gly Lys Phe Leu Lys Lys Ala Lys Lys Phe Gly Lys Ala Phe Val Lys Ile Met Lys Lys—NH₂ (SEQ ID NO: 52) |
|---|---|
| Analogue 2 | Gly Ile Gly Lys Phe Leu Lys Lys Ala Lys Lys Phe Ala Lys Ala Phe Val Lys Ile Met Lys Lys—NH₂ (SEQ ID NO: 53) |
| Analogue 3 | Gly Ile Gly Lys Phe Leu Lys Lys Ala Lys Lys Phe Ala Lys Ala Phe Val Lys Ile Ile Lys Lys—NH₂ (SEQ ID NO: 54) |

The analogues were then tested for % effective growth inhibition. Analogue 1 had % effective growth inhibitions of 100% at 1.25 µg/ml for E. Coli, 100% at 2.5 µg/ml for P. aeruginosa, and 100% at 1.25 µg/ml for S.epidermidis. Analogue 2 had % effective growth inhibitions of 100% at 2.5 µg/ml for E.Coli, 100 at 2.5 µg/ml for P.aeruginosa, and 100% at 1.25 µg/ml for S.epidermidis. Analogue 3 had % effective growth inhibitions of 100% at 1.25 µg/ml for E. Coli, 100% at 2.5 µg/ml for P.aeruginosa, and 100% at 1.25 µg/ml for S.epidermidis

EXAMPLE 24

Amide (NH₂) terminated analogues of Magainin I were synthesized wherein at least amino acid residues 17–23 were deleted and amino acid residues 3, 7, and 8 were substituted with lysine residues. The analogues had the following structures.

Analogue 1—Gly Ile Lys Lys Phe Leu Lys Lys Ala Gly Lys Phe Gly Lys-NH₂ (SEQ ID NO:3)

Analogue 2—Gly Ile Lys Lys Phe Leu Lys Lys Ala Gly Lys Phe Gly Lys Ala Phe-NH₂ (SEQ ID NO:4)

The analogues were then tested for effective growth inhibition. Analogue 1 had % effective growth inhibitions of 100% at 10 µg/ml for E. Coli, 100% at 10 µg/ml for P.aeruginosa, and 100% at 10 µg/ml for S.epidermidis. Analogue 2 had % effective growth inhibitions of 100% of 2.5 µg/ml for E. Coli, 100% at 5 µg/ml for P.aeruginosa, and 100% at 5 µg/ml for S.epidermidis.

EXAMPLE 25

Amide (NH₂)-terminated analogues of Magainin II were synthesized wherein at least amino acid residues 16–23 were deleted and substitutions were made for other residues. The analogues had the following structures.

Analogue 1—Gly Ile Lys Lys Phe Leu Lys Lys Ala Lys Lys Phe Gly Lys Ala-NH₂ (SEQ ID NO:5)

Analogue 2—Gly Ile Lys Lys Phe Leu Lys Lys Ala Lys Lys Phe Ala Lys Ala-NH₂ (SEQ ID NO:6)

The analogues were then tested for effective growth inhibition. Analogue 1 had % effective growth inhibitions of 100% at 10 µg/ml for P.aeruginosa, and 100 at 5.0 µg/ml for S.epidermidis. Analogue 2 had % effective grwoth inhibitions of 100% of 5 µg/ml, for E. Coli, 100% at 5 µg/ml for P.aeruginosa, and 100% at 5 µg/ml for S.epidermidis.

EXAMPLE 26

An amide (NH₂)-terminated analogue, which by virtue of its structure may be an analogue of Magainin I or Magainin II, was synthesized wherein amino acids 16–23 were deleted, amino acid residues 3,7, and 8 were substituted with lysine residues, and amino acid residue 10 and 13 were substituted with alanine residues. The analogue was of the following structure.

Gly Ile Lys Lys Phe Leu Lys Ala Ala Lys Phe Ala Lys Ala-NH₂ (SEQ ID NO:7)

The analogue was then tested for % effective growth inhibition. The analogue had % effective growth inhibitions of 100% at 5 µg/ml for E. Coli, 100% at 5 µg/ml for P.aeruginosa, and 100 at 5 µg/ml for S.epidermidis.

EXAMPLE 27

Analogues of Magainin II were synthesized wherein amino acid residue 19 (glutamic acid) was deleted, and amino acids 1–4, or 3,5, and 6 were deleted and at least one of the remaining amino acid residues was substituted. The analogues were of the following structures:

Analogue 1: Phe Leu Lys Ser Ala Lys Lys Phe Gly Lys Ala Phe Val Gly Ile Met Asn Ser (SEQ ID NO:20)

Analogue 2: Phe Leu Lys Ser Ala Lys Lys Phe Ala Lys Ala Phe Val Gly Ile Met Asn Ser (SEQ ID NO:21)

Analogue 3: Phe Leu His Ser Ala Lys Lys Phe Gly Lys Ala Phe Val Phe Ile Met Asn Ser (SEQ ID NO:18)

Analogue 4: Gly Ile Lys His Ser Ala Lys Lys Phe Ala Lys Ala Phe Lys Ala Ile Met Asn Ser (SEQ ID NO:19)

The analogues were then tested for % effective growth inhibition of E.coli, P.aeruginosa, and S.epidermidis. The % effective growth inhibition of each of these analogues is given in Table XIV below.

TABLE XIV

| | % Effective Growth Inhibition, Concentration in µg/ml | | |
|---|---|---|---|
| Analogue | E. Coli | P. aeruginosa | S. epidermidis |
| 1 | 100 at 25 | 100 at 25 | 100 at 50 |
| 2 | 100 at 10 | 100 at 25 | 100 at 50 |
| 3 | 100 at 25 | 100 at 25 | 100 at 10 |
| 4 | 100 at 10 | 100 at 25 | 100 at 5 |

EXAMPLE 28

Antibacterial Assay

The procedure for the following antibacterial assay is based upon the guidelines of the National Committee for Chemical Laboratory Standards, Document M7-T2, Volume 8, No. 8, 1988.

Stock solutions of the following analogues 1, 2, 3 and 4 were prepared at a concentration of 512 µg/ml in sterile deionized distilled water and stored at −70° C. Analogue 1 is an analogue of Magainin I wherein amino acid residue 19 has been deleted and residues 7, 8, 10, 18 and 23 were each substituted with a lysine residue, and amino acid residue 21 has been substituted with a leucine residue. Analogue 1 has the following structural formula:

Gly Ile Gly Lys Phe Leu Lys Lys Ala Lys Lys Phe Gly Lys Ala Phe Val Lys Ile Leu Lys Lys-NH₂ (SEQ ID NO:55)

Analogue 2 is an analogue of Magainin II wherein amino acid residue 19 has been deleted and amino acid residues 7 and 18 each are substituted with lysine, and amino acid 21 has been substituted with leucine. Analogue 2 has the following structural formula:

Gly Ile Gly Lys Phe Leu Lys Ser Ala Lys Lys Phe Gly Lys Ala Phe Val Lys Ile Leu Asn Ser-NH₂ (SEQ ID NO:56)

Analogue 3 is a derivative of Magainin II wherein amino acid residue 19 has been deleted, and amino acid residues 7 and 18 have been substituted with lysine residues. Analogue 3 has the following structural formula:

Gly Ile Gly Lys Phe Leu Lys Ser Ala Lys Lys Phe Gly Lys Ala Phe Val Lys Ile Met Asn Ser-NH₂ (SEQ ID NO:57)

Analogue 4 is a derivative of Magainin I wherein amino acid residue 19 has been deleted, and amino acid residues 7, 8, 10, 18 and 23 have been substituted with lysine, and amino acid residue 21 is a methionine sulfoxide residue. Analogue 4 has the following structural formula:

Gly Ile Gly Lys Phe Leu Lys Lys Ala Lys Lys Phe Gly Lys Ala Phe Val Lys Ile Met* Lys Lys-NH₂, wherein Met* is methionine sulfoxide. (SEQ ID NO:58)

The stock peptide solution is diluted in serial dilutions (1:2) down the wells of a microtiter plate so that the final concentration of peptides in the wells are 0.25, 0.50, 1, 2, 4, 8, 16, 32, 64, 128 and 256 µg/ml. 1–5×10⁵ CFU's/ml of either S.aureus ATCC 25923, E.coli ATCC 25922, or P.aeruginosa ATCC 27853 were added to the wells in full strength Mueller Hinton broth (BBL 11443) from a mid-log culture. The inoculum is standardized spectrophotometrically at 600 nm and is verified by colony counts. The plates are incubated for 16–20 hours at 37° C. and the minimal inhibitory concentration (MIC) of each peptide in µg/ml is determined. Where more than one MIC value appears, more than one assay was performed and different MIC values were obtained for each assay. For this assay, minimal inhibitory concentration is defined as the lowest concentration of peptide which produces a clear well in the microtiter plate. For purposes of explanation, S is the MIC of peptide nst S.aureus, P is the MIC of peptide against P.aeruginosa, and E is the MIC of peptide against E.coli. The results are given in Table XV below.

TABLE XV

| | MIC (µg/ml) | | |
|---|---|---|---|
| Analogue | S | P | E |
| 1 | 4 | 4, 8 | 8 |
| 2 | 8 | 4, 8 | 2, 4 |
| 3 | 8, 16 | 4, 8 | 2, 4 |
| 4 | 32 | 8 | 16 |

Numerous modifications and variations of the present invention are possible in light of the above teachings, and, therefore, within the scope of the accompanying claims, the invention may be practiced other than as particularly described.

What is claimed is:

1. A compound comprising: an analogue of Magainin I peptide that is in an amide- or carboxy-terminated form, and wherein Magainin I is represented by SEQ ID NO:1 and the following structural formula using the single letter amino acid code and the numbers below each amino acid residue refer to the position of the residue in the peptide:

G I G K F L H S A G K F G K A F V G E I M K S 1 2 3 4 5 6 7 8 9 10 11 12 13 14 15 16 17 18 19 20 21 22 23 and wherein said Magainin I peptide is substituted in at least one of positions 1–23, wherein the substituted amino acid residues which may be employed in each of positions 1–23 are following table:

| Residue No. | Substituted Residue |
| --- | --- |
| 1 | Lys, Ala |
| 2 | Lys, Ala, D—Ile |
| 3 | Lys, Ala, Trp |
| 4 | D—Lys, Ala |
| 5 | D—Phe, Ala, Lys, Trp |
| 6 | D—Leu, Lys, Ala |
| 7 | Lys, D—His, Ala |
| 8 | Ala, Lys, D—Ser, Trp |
| 9 | Lys, D—Ala, Trp |
| 10 | D—Lys, Lys, Ala, Trp |
| 11 | D—Lys |
| 12 | D—Phe, Lys, Trp |
| 13 | Ala, Lys, Trp |
| 14 | Ala, D—Lys |
| 15 | Lys, Trp, D—Ala |
| 16 | Ala, Lys, D—Phe |
| 17 | Ala, Lys, D—Val, Trp |
| 18 | Ala, Lys, Trp |
| 19 | Ala, Lys, D—Glu |
| 20 | D—Ile, Ala, Lys, Trp |
| 22 | Lys, Ala, D—Asn |
| 23 | D—Ser, Lys, Ala, and | wherein amino acid residue 21 is substituted with a proline residue.

2. A compound comprising:

an analogue of Magainin I peptide that is in an amide- or carboxy-terminated form, and wherein Magainin I is represented by SEQ ID NO:1 and the following structural formula using the single letter amino acid code and the numbers below each amino acid residue refer to the position of the residue in the peptide:

G I G K F L H S A G K F G K A F V G E I M K S 1 2 3
4 5 6 7 8 9 10 11 12 13 14 15 16 17 18 19 20 21 22 23 and wherein said Magainin I peptide is substituted in at least one of positions 1–23, wherein the substituted amino acid residues which may be employed in each of positions 1–23 are shown in the following table:

| Residue No. | Substituted Residue |
|---|---|
| 1 | Lys, Ala |
| 2 | Lys, Ala, D—Ile |
| 3 | Lys, Ala, Trp |
| 4 | D—Lys, Ala |
| 5 | D—Phe, Ala, Lys, Trp |
| 6 | D—Leu, Lys, Ala |
| 7 | Lys, D—His, Ala |
| 8 | Ala, Lys, D—Ser, Trp |
| 9 | Lys, D—Ala, Trp |
| 10 | D—Lys, Lys, Ala, Trp |
| 11 | D—Lys |
| 12 | D—Phe, Lys, Trp |
| 13 | Ala, Lys, Trp |
| 14 | Ala, D—Lys |
| 15 | Lys, Trp, D—Ala |
| 16 | Ala, Lys, D—Phe |
| 17 | Ala, Lys, D—Val, Trp |
| 18 | Ala, Lys, Trp |
| 19 | Ala, Lys, D—Glu |
| 20 | D—Ile, Ala, Lys, Trp |
| 21 | Lys, Pro, Ala |
| 22 | Lys, Ala, D—Asn |
| 23 | D—Ser, Lys, Ala, and | at least one of amino acid residues 3, 5, 8, 10, 12, 13, 15, 18 and 20 is a protected tryptophan residue.

3. A compound comprising:

an analogue of Magainin I peptide that is in an amide- or carboxy-terminated form, and wherein Magainin I is represented by SEQ ID NO:1 and the following structural formula using the single letter amino acid code and the numbers below each amino acid residue refer to the position of the residue in the peptide:

G I G K F L H S A G K F G K A F V G E I M K S 1 2 3
4 5 6 7 8 9 10 11 12 13 14 15 16 17 18 19 20 21 22 23 and wherein said Magainin I peptide is substituted in at least one of positions 1–23, wherein the substituted amino acid residues which may be employed in each of positions 1–23 are shown in the following table:

| Residue No. | Substituted Residue |
|---|---|
| 1 | Lys, Ala |
| 2 | Lys, Ala, D—Ile |
| 3 | Lys, Ala, Trp |
| 4 | D—Lys, Ala |
| 5 | D—Phe, Ala, Lys, Trp |
| 6 | D—Leu, Lys, Ala |
| 7 | Lys, D—His, Ala |
| 8 | Ala, Lys, D—Ser, Trp |
| 9 | Lys, D—Ala, Trp |
| 10 | D—Lys, Lys, Ala, Trp |
| 11 | D—Lys |
| 12 | D—Phe, Lys, Trp |
| 13 | Ala, Lys, Trp |
| 14 | Ala, D—Lys |
| 15 | Lys, Trp, D—Ala |
| 16 | Ala, Lys, D—Phe |
| 17 | Ala, Lys, D—Val, Trp |
| 18 | Ala, Lys, Trp |
| 19 | Ala, Lys, D—Glu |
| 20 | D—Ile, Ala, Lys, Trp |
| 21 | Lys, Pro, Ala |
| 22 | Lys, Ala, D—Asn |
| 23 | D—Ser, Lys, Ala, and | at least one of amino acid residues 9, 13, 15, and 17 is an unprotected tryptophan residue.

4. A compound comprising:

an analogue of Magainin II peptide that is in an amide- or carboxy-terminated form, and wherein Magainin II is represented by SEQ ID NO:2 and the following structural formula using the single letter amino acid code and the numbers below each amino acid residue refer to the position of the residue in the peptide:

G I G K F L H S A K K F G K A F V G E I M N S 1 2 3
4 5 6 7 8 9 10 11 12 13 14 15 16 17 18 19 20 21 22 23 and wherein said Magainin II peptide is substituted in at least one of positions 1–23, wherein the substituted amino acid residues which may be employed in each of positions 1–23 are shown in the following table:

| Residue No. | Substituted Residue |
|---|---|
| 1 | Lys, Ala |
| 2 | Lys, Ala, D—Ile |
| 3 | Lys, Ala, Trp |
| 4 | D—Lys, Ala |
| 5 | D—Phe, Ala, Lys, Trp |
| 6 | D—Leu, Lys, Ala |
| 7 | Lys, D—His, Ala |
| 8 | Ala, Lys, D—Ser, Trp |
| 9 | Lys, D—Ala, Trp |
| 10 | D—Lys, Lys, Ala, Trp |
| 11 | D—Lys |
| 12 | D—Phe, Lys, Trp |
| 13 | Ala, Lys, Trp |
| 14 | Ala, D—Lys |
| 15 | Lys, Trp, D—Ala |
| 16 | Ala, Lys, D—Phe |
| 17 | Ala, Lys, D—Val, Trp |
| 18 | Ala, Lys, Trp |
| 19 | Ala, Lys, D—Glu |
| 20 | D—Ile, Ala, Lys, Trp |
| 21 | Lys, Pro, Ala |
| 22 | Lys, Ala, D—Asn |
| 23 | D—Ser, Lys, Ala, and | at least one of amino acid residues 1–3, 5–9, 12, 13, or 15–23 is a lysine residue.

5. A compound comprising:

an analogue of Magainin I peptide that is in an amide- or carboxy-terminated form, wherein Magainin I is represented by SEQ ID NO:1 and the following structural formula using the single letter amino acid code and the numbers below each amino acid residue refer to the position of the residue in the peptide:

G I G K F L H S A G K F G K A F V G E I M K S 1 2 3
4 5 6 7 8 9 10 11 12 13 14 15 16 17 18 19 20 21 22 23, and wherein said Magainin I peptide is substituted in at least one of positions 1–15 wherein the substituted amino acid residues which may be employed in each of positions 1–15 are shown in the following table:

| Residue No. | Substituted Residue |
|---|---|
| 1 | Lys, Ala |
| 2 | Lys, Ala, D—Ile |
| 4 | D—Lys, Ala |
| 5 | D—Phe, Ala, Lys, Trp |
| 6 | D—Leu, Lys, Ala |
| 7 | Lys, D—His, Ala |
| 9 | Lys, D—Ala, Trp |
| 11 | D—Lys |
| 12 | D—Phe, Lys, Trp |
| 13 | Ala, Lys, Trp |
| 14 | Ala, D—Lys |
| 15 | Lys, Trp, D—Ala and | amino acid residues 16–23 are deleted and amino acid residues 3, 8 and 10 are substituted with an alanine residue.

6. A compound comprising:

an analogue of Magainin I peptide that is in an amide- or carboxy-terminated form, wherein Magainin I is represented by SEQ ID NO:1 and the following structural formula using the single letter amino acid code and the numbers below each amino acid residue refer to the position of the residue in the peptide:

G I G K F L H S A G K F G K A F V G E I M K S 1 2 3 4 5 6 7 8 9 10 11 12 13 14 15 16 17 18 19 20 21 22 23, and wherein at least one of amino acid residues 15–23 is omitted, and wherein said Magainin I peptide is substituted in at least one of the remaining positions 1–23, wherein the substituted amino acid residues which may be employed in each of positions 1–23 are shown in the following table:

| Residue No. | Substituted Residue |
|---|---|
| 1 | Lys, Ala |
| 2 | Lys, Ala, D—Ile |
| 3 | Lys, Ala, Trp |
| 4 | D—Lys, Ala |
| 5 | Lys |
| 6 | D—Leu, Lys, Ala |
| 7 | Lys, D—His, Ala |
| 8 | Lys |
| 9 | Lys |
| 10 | D—Lys, Lys, Ala, Trp |
| 11 | D—Lys |
| 12 | D—Phe, Lys, Trp |
| 13 | Ala, Lys, Trp |
| 14 | Ala, D—Lys |
| 15 | Lys, Trp, D—Ala |
| 16 | Lys |
| 17 | Ala, Lys, D—Val, Trp |
| 18 | Ala |
| 20 | D—Ile, Ala, Lys, Trp |
| 21 | Leu |
| 22 | Lys, Ala, D—Asn |
| 23 | Ala, and | wherein amino acid residue 19 is deleted, amino acid residues 5, 8, 9 and 16 are each substituted with a lysine residue, and amino acid residue 21 is substituted with a leucine residue, and amino acid residues 18 and 23 are each substituted with an alanine residue.

7. A compound comprising:

an analogue of Magainin I peptide that is in an amide- or carboxy-terminated form, wherein Magainin I is represented by SEQ ID NO:1 and the following structural formula using the single letter amino acid code and the numbers below each amino acid residue refer to the position of the residue in the peptide:

G I G K F L H S A G K F G K A F V G E I M K S 1 2 3 4 5 6 7 8 9 10 11 12 13 14 15 16 17 18 19 20 21 22 23, and wherein said Magainin I peptide is substituted in at least one of the remaining positions 1–23, wherein the substituted amino acid residues which may be employed in each of positions 1–23 are shown in the following table:

| Residue No. | Substituted Residue |
|---|---|
| 1 | Lys, Ala |
| 2 | Lys, Ala, D—Ile |
| 3 | Lys, Ala, Trp |
| 4 | D—Lys, Ala |
| 5 | Lys |
| 6 | D—Leu, Lys, Ala |
| 7 | Phe |
| 8 | Ala, Lys, D—Ser, Trp |
| 9 | Lys, D—Ala, Trp |
| 10 | Lys |
| 11 | D—Lys |
| 12 | D—Phe, Lys, Trp |
| 13 | Ala, Lys, Trp |
| 14 | Ala, D—Lys |
| 15 | Lys, Trp, D—Ala |
| 16 | Ala, Lys, D—Phe |
| 17 | Ala, Lys, D—Val, Trp |
| 18 | Lys |
| 19 | Lys |
| 20 | D—Ile, Ala, Lys, Trp |
| 22 | Ala |
| 23 | D—Ser, Lys, Ala, and | wherein amino acid residue 21 is deleted, amino acid residues 5, 10, 18, and 19 are each substituted with a lysine residue, amino acid 7 is substituted with a phenylalanine residue, and amino acid residue 22 is substituted with an alanine residue.

8. A compound comprising:

an analogue of Magainin I or Magainin II peptide, said Magainin I peptide or Magainin II peptide being in an amide- or carboxy-terminated form, wherein Magainin I is represented by SEQ ID NO:1 and the following structural formula using the single letter amino acid code and the numbers below each amino acid residue refer to the position of the residue in the peptide:

G I G K F L H S A G K F G K A F V G E I M K S 1 2 3 4 5 6 7 8 9 10 11 12 13 14 15 16 17 18 19 20 21 22 23, and wherein Magainin II is represented by SEQ ID NO:2 and the following structural formula using the single letter amino acid code and the numbers below each amino acid residue refer to the position of the residue in the peptide:

G I G K F L H S A K K F G K A F V G E I M N S 1 2 3 4 5 6 7 8 9 10 11 12 13 14 15 16 17 18 19 20 21 22 23, wherein amino acids 17–23 or 16–23 or 15–23 are deleted, and amino acids, 3,7, and 8 are substituted with a lysine residue.

9. The compound of claim 8 wherein said analogue of Magainin I or Magainin II peptide is selected from the group consisting of:

GIKKFLKKAGKFGK-NH$_2$ (SEQ ID NO:3);
GIKKFLKKAGKFGKAF-NH$_2$ (SEQ ID NO:4);
GIKKFLKKAKKFGKA-NH$_2$ (SEQ ID NO:5);
GIKKFLKKAKKFAKA-NH$_2$ (SEQ ID NO:6); and
GIKKFLKKAAKFAKA-NH$_2$ (SEQ ID NO:7).

10. A compound comprising: an analogue of Magainin I peptide or Magainin II peptide, said Magainin I peptide or Magainin II peptide that is in an amide- or carboxy-terminated form, and wherein Magainin I is represented by SEQ ID NO:1 and the following structural formula using the single letter amino acid code and the numbers below each amino acid residue refer to the position of the residue in the peptide:

G I G K F L H S A G K F G K A F V G E I M K S
1 2 3 4 5 6 7 8 9 10 11 12 13 14 15 16 17 18 19 20 21 22 23, and wherein Magainin II is represented by SEQ ID NO:2 and the following structural formula using the single letter amino acid code and the numbers below each amino acid residue refer to the position of the residue in the peptide:

G I G K F L H S A K K F G K A F V G E I M N S
1 2 3 4 5 6 7 8 9 10 11 12 13 14 15 16 17 18 19 20 21 22 23, wherein amino acid residue 19 is omitted, and either amino acid residues 1–4 are omitted or amino acid residues 3, 5, and 6 are omitted.

11. The compound of claim 10 wherein the peptide is a Magainin II peptide.

12. A peptide that is selected from the group consisting of:
FLHSAKKFGKAFVFIMNS (SEQ ID NO:18);
GIKHSAKKFAKAFKAIMNS (SEQ ID NO:19);
FLKSAKKFGKAFVGIMNS (SEQ ID NO:20); and
FLKSAKKFAKAFVGIMNS (SEQ ID NO:21).

13. A peptide that has the following structural formula:
G I G K F L K K A K K F G K A F V K I M K K-NH₂ (SEQ ID NO:52).

14. A peptide that is selected from the class consisting of:
G I G K F L K K A K K F G K A F V K I L K K-NH₂ (SEQ ID NO:55);
G I G K F L K K A K K F A K A F V K I I N N-NH₂ (SEQ ID NO: 50;
G I G K F L K S A K K F G K A F V K I L N S-NH₂ (SEQ ID NO:56); and
G I G K F L K S A K K F G K A F V K I M N S-NH₂ (SEQ ID NO:57).

15. A peptide that has the following structural formula:
G I G K F L K K A K K F G K A F V K I L K K-NH₂ (SEQ ID NO:55).

16. A peptide that has the following structural formula:
G I G K F L K K A K K F G K A F V K I M*K K-NH₂, wherein M* is a methionine sulfoxide residue (SEQ ID NO:58).

17. A process for inhibiting growth or proliferation of microbes in an infected host comprising
administering to said infected host a compound of claim 2 in an effective growth or proliferation-inhibiting amount.

18. A process for inhibiting growth or proliferation of microbes in an infected host comprising
administering to said infected host a compound of claim 14 in an effective growth or proliferation-inhibiting amount.

19. The process according to claim 18 wherein said compound has SEQ ID NO:55.

20. A compound comprising:
an analogue of Magainin I peptide that is in an amide- or carboxy-terminated form, and wherein Magainin I is represented by SEQ ID NO:1 and the following structural formula using the single letter amino acid code and the numbers below each amino acid residue refer to the position of the residue in the peptide:

G I G K F L H S A G K F G K A F V G E I M K S
1 2 3 4 5 6 7 8 9 10 11 12 13 14 15 16 17 18 19 20 21 22 23 and wherein said Magainin I peptide is substituted in at least one of positions 1–23, wherein the substituted amino which may be employed in each of positions 1–23 are following table:

| Residue No. | Substituted Residue |
|---|---|
| 1 | Lys, Ala |
| 2 | Lys, Ala, D—Ile |
| 3 | Lys |
| 4 | D—Lys, Ala |
| 5 | D—Phe, Ala, Lys, Trp |
| 6 | D—Leu, Lys, Ala |
| 7 | Lys, D—His, Ala |
| 8 | Lys |
| 9 | Lys |
| 10 | D—Lys, Lys, Ala, Trp |
| 11 | D—Lys |
| 12 | D—Phe, Lys, Trp |
| 13 | Ala, Lys, Trp |
| 14 | Ala, D—Lys |
| 15 | Lys, Trp, D—Ala |
| 16 | Ala |
| 17 | Ala, Lys, D—Val, Trp |
| 18 | Ala, Lys, Trp |
| 19 | Lys |
| 20 | D—Ile, Ala, Lys, Trp |
| 21 | Lys, Pro, Ala |
| 22 | Ala, D—Asn |
| 23 | Lys | wherein amino acid residues 3, 8, 9, 19 and 23 are each substituted with a lysine residue and amino acid residue 16 is substituted with an alanine residue.

21. A process for inhibiting tumor growth in a host comprising
administering to a host having a tumor an effective tumor-inhibiting amount of a compound that is an analogue of a Magainin II peptide that is in an amide- or carboxy-terminated form,
and wherein Magainin II is represented by SEQ ID NO:2 and the following structural formula using the single letter amino acid code and the numbers below each amino acid residue refer to the position of the residue in the peptide:

G I G K F L H S A K K F G K A F V G E I M N S
1 2 3 4 5 6 7 8 9 10 11 12 13 14 15 16 17 18 19 20 21 22 23, wherein amino acid residue 19 is omitted, and at least one of amino acid residues 3, 7, 8, 10, 13, 15, 16, 18, 21, 22, or 23 is substituted with another amino acid residue as shown in the following table:

| Residue No. | Substituent |
|---|---|
| 3 | Leu |
| 7 | Lys |
| 8 | Lys, Ala |
| 10 | Ala |
| 13 | Trp, Phe, Leu, Ala |
| 15 | Phe |
| 16 | Ala |
| 18 | Lys, Ala, Phe |
| 21 | Lys, Ile, Leu |
| 22 | Lys |
| 23 | Lys, D—Ser, Asn. |

22. A process for inhibiting tumor growth in a host comprising
administering to a host having a tumor an effective tumor-inhibiting amount of a compound that is selected from the group consisting of:

G I G K F L K K A K K F G K A F V K I L K K-NH$_2$ (SEQ ID NO:55);

G I G K F L K K A K K F A K A F V K I I N N-NH$_2$ (SEQ ID NO:50);

G I G K F L K S A K K F G K A F V K I L N S-NH$_2$ (SEQ ID NO:56); and

G I G K F L K S A K K F G K A F V K I M N S-NH$_2$ (SEQ ID NO:57).

23. The process according to claim 22 wherein said compound has SEQ ID NO:55.

24. An antibacterial composition comprising an antibacterial amount of a polypeptide of SEQ ID NO:55 in combination with a non-toxic pharmaceutical carrier.

25. The antibacterial composition according to claim 24 wherein said composition is adapted for topical use.

26. The antibacterial composition according to claim 25 wherein said polypeptide is used at a concentration of about 0.5 to about 5 percent.

* * * * *

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
      (A) LENGTH: 23 amino acids
      (B) TYPE: amino acid
      (D) TOPOLOGY: linear (ii) MOLECULE TYPE: peptide (xi) SEQUENCE DESCRIPTION: SEQ ID NO:1:

```
     Gly Ile Gly Lys Phe Leu His Ser Ala Gly Lys Phe Gly Lys Ala Phe
     1               5                   10                  15

Val Gly Glu Ile Met Lys Ser
                 20
```

(2) INFORMATION FOR SEQ ID NO:2:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:2:

```
     Gly Ile Gly Lys Phe Leu His Ser Ala Lys Lys Phe Gly Lys Ala Phe
     1               5                   10                  15

Val Gly Glu Ile Met Asn Ser
                 20
```

(2) INFORMATION FOR SEQ ID NO:3:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 14
        (D) OTHER INFORMATION: /note= "Xaa=lysine amide"

(xi) SEQUENCE DESCRIPTION: SEQ ID NO:3:

```
     Gly Ile Lys Lys Phe Leu Lys Lys Ala Gly Lys Phe Gly Xaa
     1               5                   10
```

(2) INFORMATION FOR SEQ ID NO:4:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 16
        (D) OTHER INFORMATION: /note= "Xaa=phenylalanine amide"

(xi) SEQUENCE DESCRIPTION: SEQ ID NO:4:

```
     Gly Ile Lys Lys Phe Leu Lys Lys Ala Gly Lys Phe Gly Lys Ala Xaa
     1               5                   10                  15
```

(2) INFORMATION FOR SEQ ID NO:5:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 15
        (D) OTHER INFORMATION: /note= "Xaa=alanine amide"

(xi) SEQUENCE DESCRIPTION: SEQ ID NO:5:

Gly Ile Lys Lys Phe Leu Lys Lys Ala Lys Lys Phe Gly Lys Xaa
1               5                   10                  15

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 15
        (D) OTHER INFORMATION: /note= "Xaa=alanine amide"

(xi) SEQUENCE DESCRIPTION: SEQ ID NO:6:

Gly Ile Lys Lys Phe Leu Lys Lys Ala Lys Phe Ala Lys Xaa
1               5                   10                  15

(2) INFORMATION FOR SEQ ID NO:7:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 15
        (D) OTHER INFORMATION: /note= "Xaa=alanine amide"

(xi) SEQUENCE DESCRIPTION: SEQ ID NO:7:

Gly Ile Lys Lys Phe Leu Lys Lys Ala Ala Lys Phe Ala Lys Xaa
1               5                   10                  15

(2) INFORMATION FOR SEQ ID NO:8:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:8:

Gly Ile Gly Lys Phe Leu His Ser Ala Lys Lys Phe Gly Lys Ala Phe
1               5                   10                  15

Val Gly Ile Met Lys Ser
            20

(2) INFORMATION FOR SEQ ID NO:9:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:9:

Gly Ile Gly Lys Phe Leu His Ser Ala Lys Lys Phe Gly Lys Ala Phe
1               5                   10                  15

Val Ala Ile Met Lys Ser
            20

(2) INFORMATION FOR SEQ ID NO:10:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 22
        (D) OTHER INFORMATION: /note= "Xaa=D-serine"

(xi) SEQUENCE DESCRIPTION: SEQ ID NO:10:

```
Gly Ile Gly Lys Phe Leu His Ser Ala Lys Lys Phe Gly Lys Ala Phe
1               5                  10                  15

Val Phe Ile Met Asn Xaa
            20
```

(2) INFORMATION FOR SEQ ID NO:11:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:11:

```
Gly Ile Gly Lys Phe Leu His Ser Ala Lys Lys Phe Phe Lys Ala Phe
1               5                  10                  15

Val Phe Ile Met Asn Ser
            20
```

(2) INFORMATION FOR SEQ ID NO:12:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:12:

```
Gly Ile Gly Lys Phe Leu Lys Ser Ala Lys Lys Phe Gly Lys Ala Phe
1               5                  10                  15

Val Phe Ile Met Asn Ser
            20
```

(2) INFORMATION FOR SEQ ID NO:13:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:13:

```
Gly Ile Gly Lys Phe Leu His Lys Ala Lys Lys Phe Ala Lys Ala Phe
1               5                  10                  15

Val Phe Ile Met Asn Ser
            20
```

(2) INFORMATION FOR SEQ ID NO:14:

```
    (i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:14:

Gly Ile Gly Lys Phe Leu Lys Ser Ala Lys Lys Phe Ala Lys Ala Phe
  1               5                  10                  15

Val Phe Ile Met Asn Ser
              20

(2) INFORMATION FOR SEQ ID NO:15:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:15:

Gly Ile Gly Lys Phe Leu His Lys Ala Lys Lys Phe Ala Lys Ala Phe
  1               5                  10                  15

Val Phe Ile Met Asn Lys
              20

(2) INFORMATION FOR SEQ ID NO:16:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:16:

Gly Ile Gly Lys Phe Leu Lys Lys Ala Lys Lys Phe Gly Lys Ala Phe
  1               5                  10                  15

Val Phe Ile Met Lys Lys
              20

(2) INFORMATION FOR SEQ ID NO:17:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 18
        (D) OTHER INFORMATION: /note= "Xaa=epsilon-Fmoc-lysine"

(xi) SEQUENCE DESCRIPTION: SEQ ID NO:17:

Gly Ile Gly Lys Phe Leu His Ser Ala Lys Lys Phe Gly Lys Ala Phe
  1               5                  10                  15

Val Xaa Ile Met Asn Ser
              20

(2) INFORMATION FOR SEQ ID NO:18:

(i) SEQUENCE CHARACTERISTICS:
        (A) LENGTH: 18 amino acids
```

(B) TYPE: amino acid
            (D) TOPOLOGY: linear (ii) MOLECULE TYPE: peptide (xi) SEQUENCE DESCRIPTION: SEQ ID NO:18:

Phe Leu His Ser Ala Lys Lys Phe Gly Lys Ala Phe Val Phe Ile Met
    1               5                   10                  15

Asn Ser (2) INFORMATION FOR SEQ ID NO:19:

(i) SEQUENCE CHARACTERISTICS:
            (A) LENGTH: 19 amino acids
            (B) TYPE: amino acid
            (D) TOPOLOGY: linear (ii) MOLECULE TYPE: peptide (xi) SEQUENCE DESCRIPTION: SEQ ID NO:19:

Gly Ile Lys His Ser Ala Lys Lys Phe Ala Lys Ala Phe Lys Ala Ile
    1               5                   10                  15

Met Asn Ser (2) INFORMATION FOR SEQ ID NO:20:

(i) SEQUENCE CHARACTERISTICS:
            (A) LENGTH: 18 amino acids
            (B) TYPE: amino acid
            (D) TOPOLOGY: linear (ii) MOLECULE TYPE: peptide (xi) SEQUENCE DESCRIPTION: SEQ ID NO:20:

Phe Leu Lys Ser Ala Lys Lys Phe Gly Lys Ala Phe Val Gly Ile Met
    1               5                   10                  15

Asn Ser (2) INFORMATION FOR SEQ ID NO:21:

(i) SEQUENCE CHARACTERISTICS:
            (A) LENGTH: 18 amino acids
            (B) TYPE: amino acid
            (D) TOPOLOGY: linear (ii) MOLECULE TYPE: peptide (xi) SEQUENCE DESCRIPTION: SEQ ID NO:21:

Phe Leu Lys Ser Ala Lys Lys Phe Ala Lys Ala Phe Val Gly Ile Met
    1               5                   10                  15

Asn Ser (2) INFORMATION FOR SEQ ID NO:22:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (xi) SEQUENCE DESCRIPTION: SEQ ID NO:22:

Gly Ile Gly Lys Lys Leu His Lys Lys Gly Lys Phe Gly Lys Phe Lys
    1               5                   10                  15

Gly Ala Ile Leu Lys Ala
                20

(2) INFORMATION FOR SEQ ID NO:23:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:23:

```
Gly Ile Gly Lys Lys Leu Phe Ser Ala Lys Lys Phe Gly Lys Ala Phe
1               5                   10                  15

Val Lys Lys Ile Ala Ser
            20
```

(2) INFORMATION FOR SEQ ID NO:24:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:24:

```
Gly Ile Ala Lys Phe Leu His Ala Ala Gly Lys Phe Gly Lys Ala Ala
1               5                   10                  15

Val Gly Ala Ile Met Lys Ala
            20
```

(2) INFORMATION FOR SEQ ID NO:25:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:25:

```
Gly Ile Ala Lys Phe Leu His Ala Ala Gly Lys Phe Gly Lys Ala Ala
1               5                   10                  15

Val Gly Ala Ile Met Lys Lys
            20
```

(2) INFORMATION FOR SEQ ID NO:26:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:26:

```
Gly Ile Ala Lys Phe Leu His Ala Ala Gly Lys Phe Gly Lys Ala Ala
1               5                   10                  15

Val Gly Lys Ile Met Lys Ala
            20
```

(2) INFORMATION FOR SEQ ID NO:27:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:27:

Gly Ile Ala Lys Phe Leu His Ala Lys Gly Lys Phe Gly Lys Ala Ala
    1               5                   10                  15

Val Gly Ala Ile Met Lys Ala
                20

(2) INFORMATION FOR SEQ ID NO:28:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:28:

Gly Ile Ala Lys Phe Leu His Lys Ala Gly Lys Phe Gly Lys Ala Ala
    1               5                   10                  15

Val Gly Ala Ile Met Lys Ala
                20

(2) INFORMATION FOR SEQ ID NO:29:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:29:

Gly Ile Lys Lys Phe Leu His Ala Ala Gly Lys Phe Gly Lys Ala Ala
    1               5                   10                  15

Val Gly Ala Ile Met Lys Ala
                20

(2) INFORMATION FOR SEQ ID NO:30:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:30:

Gly Ile Lys Lys Phe Leu His Lys Lys Gly Lys Phe Gly Lys Ala Ala
    1               5                   10                  15

Val Gly Lys Ile Met Lys Lys
                20

(2) INFORMATION FOR SEQ ID NO:31:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:31:

Gly Ile Gly Lys Phe Leu His Ser Ala Gly Lys Phe Gly Lys Ala Ala
    1               5                   10                  15

Val Gly Ile Met Lys Ser
                    20

(2) INFORMATION FOR SEQ ID NO:32:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:32:

Gly Ile Gly Lys Phe Leu His Ser Ala Ala Lys Phe Gly Lys Ala Phe
        1               5                   10                  15

Val Gly Ile Met Lys Ser
                    20

(2) INFORMATION FOR SEQ ID NO:33:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:33:

Gly Ile Gly Lys Phe Leu His Ala Ala Gly Lys Phe Gly Lys Ala Phe
        1               5                   10                  15

Val Gly Ile Met Lys Ser
                    20

(2) INFORMATION FOR SEQ ID NO:34:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:34:

Gly Ile Gly Lys Phe Leu His Ser Ala Gly Lys Phe Gly Lys Ala Phe
        1               5                   10                  15

Val Lys Ile Met Lys Ser
                    20

(2) INFORMATION FOR SEQ ID NO:35:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:35:

Gly Ile Gly Lys Phe Leu His Lys Ala Gly Lys Phe Gly Lys Ala Phe
        1               5                   10                  15

Val Gly Ile Met Lys Ser
                    20

(2) INFORMATION FOR SEQ ID NO:36:

(i) SEQUENCE CHARACTERISTICS:
        (A) LENGTH: 22 amino acids (B) TYPE: amino acid
            (D) TOPOLOGY: linear (ii) MOLECULE TYPE: peptide (xi) SEQUENCE DESCRIPTION: SEQ ID NO:36:

Gly Ile Gly Lys Phe Leu Lys Ser Ala Gly Lys Phe Gly Lys Ala Phe
    1               5                   10                  15

Val Gly Ile Met Lys Ser
                20

(2) INFORMATION FOR SEQ ID NO:37:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:37:

Gly Ile Lys Lys Phe Leu Lys Lys Ala Gly Lys Phe Gly Lys Ala
    1               5                   10                  15

(2) INFORMATION FOR SEQ ID NO:38:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:38:

Gly Ile Ala Lys Phe Leu His Ala Ala Lys Phe Gly Lys Ala
    1               5                   10                  15

(2) INFORMATION FOR SEQ ID NO:39:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:39:

Gly Ile Gly Lys Phe Leu His Ser Ala Lys Lys Phe Trp Lys Ala Phe
    1               5                   10                  15

Val Gly Ile Met Asn Ser
                20

(2) INFORMATION FOR SEQ ID NO:40:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:40:

Gly Ile Gly Lys Phe Leu His Ser Ala Lys Lys Phe Leu Lys Ala Phe
    1               5                   10                  15

Val Gly Ile Leu Asn Ser
                20

(2) INFORMATION FOR SEQ ID NO:41:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:41:

Gly Ile Leu Lys Phe Leu His Ser Ala Lys Lys Phe Leu Lys Ala Phe
    1                5                      10                  15

Val Gly Ile Leu Asn Ser
                20

(2) INFORMATION FOR SEQ ID NO:42:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:42:

Gly Ile Leu Lys Phe Leu His Ser Ala Lys Lys Phe Phe Lys Ala Phe
    1                5                      10                  15

Val Lys Ile Leu Asn Ser
                20

(2) INFORMATION FOR SEQ ID NO:43:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:43:

Gly Ile Gly Lys Phe Leu His Ser Ala Lys Lys Phe Phe Lys Ala Phe
    1                5                      10                  15

Val Phe Ile Leu Asn Ser
                20

(2) INFORMATION FOR SEQ ID NO:44:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:44:

Gly Ile Gly Lys Phe Leu His Ser Ala Lys Lys Phe Ala Lys Ala Phe
    1                5                      10                  15

Val Phe Ile Met Asn Ser
                20

(2) INFORMATION FOR SEQ ID NO:45:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:45:

Gly Ile Gly Lys Phe Leu His Lys Ala Lys Lys Phe Phe Lys Ala Phe
1               5                   10                  15

Val Phe Ile Met Asn Ser
            20

(2) INFORMATION FOR SEQ ID NO:46:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:46:

Gly Ile Gly Lys Phe Leu Lys Ser Ala Lys Lys Phe Phe Lys Ala Phe
1               5                   10                  15

Val Phe Ile Met Asn Ser
            20

(2) INFORMATION FOR SEQ ID NO:47:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:47:

Gly Ile Gly Lys Phe Leu Lys Ser Ala Lys Lys Phe Ala Lys Phe Phe
1               5                   10                  15

Val Phe Ile Met Asn Lys
            20

(2) INFORMATION FOR SEQ ID NO:48:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:48:

Gly Ile Gly Lys Phe Leu His Ser Ala Lys Lys Phe Gly Lys Ala Phe
1               5                   10                  15

Val Lys Ile Met Asn Ser
            20

(2) INFORMATION FOR SEQ ID NO:49:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:49:

Gly Ile Gly Lys Phe Leu His Lys Ala Lys Lys Phe Gly Lys Ala Phe
1               5                   10                  15

Val Lys Ile Met Asn Ser
            20

(2) INFORMATION FOR SEQ ID NO:50:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 22
        (D) OTHER INFORMATION: /note= "Xaa=asparagine amide"

(xi) SEQUENCE DESCRIPTION: SEQ ID NO:50:

```
Gly Ile Gly Lys Phe Leu Lys Lys Ala Lys Phe Ala Lys Ala Phe
 1               5                  10                  15

Val Lys Ile Ile Asn Xaa
                 20
```

(2) INFORMATION FOR SEQ ID NO:51:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 22
        (D) OTHER INFORMATION: /note= "Xaa=asparagine amide"

(xi) SEQUENCE DESCRIPTION: SEQ ID NO:51:

```
Gly Ile Gly Lys Phe Leu Lys Lys Ala Ala Lys Phe Ala Lys Ala Phe
 1               5                  10                  15

Val Lys Ile Ile Asn Xaa
                 20
```

(2) INFORMATION FOR SEQ ID NO:52:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 22
        (D) OTHER INFORMATION: /note= "Xaa=lysine amide"

(xi) SEQUENCE DESCRIPTION: SEQ ID NO:52:

```
Gly Ile Gly Lys Phe Leu Lys Lys Ala Lys Phe Gly Lys Ala Phe
 1               5                  10                  15

Val Lys Ile Met Lys Xaa
                 20
```

(2) INFORMATION FOR SEQ ID NO:53:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
    (A) NAME/KEY: Modified-site
    (B) LOCATION: 22
    (D) OTHER INFORMATION: /note= "Xaa=lysine amide"

(xi) SEQUENCE DESCRIPTION: SEQ ID NO:53:

Gly Ile Gly Lys Phe Leu Lys Lys Ala Lys Lys Phe Ala Lys Ala Phe
1               5                   10                  15

Val Lys Ile Met Lys Xaa
            20

(2) INFORMATION FOR SEQ ID NO:54:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 22
        (D) OTHER INFORMATION: /note= "Xaa=lysine amide"

(xi) SEQUENCE DESCRIPTION: SEQ ID NO:54:

Gly Ile Gly Lys Phe Leu Lys Lys Ala Lys Lys Phe Ala Lys Ala Phe
1               5                   10                  15

Val Lys Ile Ile Lys Xaa
            20

(2) INFORMATION FOR SEQ ID NO:55:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 22
        (D) OTHER INFORMATION: /note= "Xaa=lysine amide"

(xi) SEQUENCE DESCRIPTION: SEQ ID NO:55:

Gly Ile Gly Lys Phe Leu Lys Lys Ala Lys Lys Phe Gly Lys Ala Phe
1               5                   10                  15

Val Lys Ile Leu Lys Xaa
            20

(2) INFORMATION FOR SEQ ID NO:56:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 22
        (D) OTHER INFORMATION: /note= "Xaa=serine aminde"

(xi) SEQUENCE DESCRIPTION: SEQ ID NO:56:

Gly Ile Gly Lys Phe Leu Lys Ser Ala Lys Lys Phe Gly Lys Ala Phe
1               5                   10                  15

Val Lys Ile Leu Asn Xaa

20

(2) INFORMATION FOR SEQ ID NO:57:

(i) SEQUENCE CHARACTERISTICS:
      (A) LENGTH: 22 amino acids
      (B) TYPE: amino acid
      (D) TOPOLOGY: linear (ii) MOLECULE TYPE: peptide (ix) FEATURE:
      (A) NAME/KEY: Modified-site
      (B) LOCATION: 22
      (D) OTHER INFORMATION: /note= "Xaa=serine amide"

(xi) SEQUENCE DESCRIPTION: SEQ ID NO:57:

Gly Ile Gly Lys Phe Leu Lys Ser Ala Lys Lys Phe Gly Lys Ala Phe
  1               5                   10                  15

Val Lys Ile Met Asn Xaa
              20

(2) INFORMATION FOR SEQ ID NO:58:

(i) SEQUENCE CHARACTERISTICS:
      (A) LENGTH: 22 amino acids
      (B) TYPE: amino acid
      (D) TOPOLOGY: linear (ii) MOLECULE TYPE: peptide (ix) FEATURE:
      (A) NAME/KEY: Modified-site
      (B) LOCATION: 20
      (D) OTHER INFORMATION: /note= "Xaa=methionine sulfoxide"

(ix) FEATURE:
      (A) NAME/KEY: Modified-site
      (B) LOCATION: 22
      (D) OTHER INFORMATION: /note= "Xaa=lysine amide"

(xi) SEQUENCE DESCRIPTION: SEQ ID NO:58:

Gly Ile Gly Lys Phe Leu Lys Lys Ala Lys Lys Phe Gly Lys Ala Phe
  1               5                   10                  15

Val Lys Ile Xaa Lys Xaa
              20